United States Patent [19]

Ohyama et al.

[11] 4,391,804
[45] Jul. 5, 1983

[54] IMIDAZOLE DERIVATIVES AND FUNGICIDAL COMPOSITION CONTAINING THE SAME

[75] Inventors: Hiroshi Ohyama, Chigasaki; Ken Morita, Hiratsuka; Takuo Wada, Hatano; Masahiko Miyahara, Atsugi, all of Japan

[73] Assignee: Hokko Chemical Industry Company, Ltd., Japan

[21] Appl. No.: 358,533

[22] Filed: Mar. 16, 1982

[51] Int. Cl.³ .................. A01N 55/02; A01N 43/50; C07D 233/61
[52] U.S. Cl. ........................ 424/245; 424/273 R; 542/413; 542/414; 542/423; 542/422; 542/426; 548/107; 548/336; 548/341
[58] Field of Search ............ 548/107, 336, 341; 542/413, 414, 423, 426, 422; 424/273 R, 245

[56] References Cited

U.S. PATENT DOCUMENTS 4,187,302  2/1980  Ikuru et al. ................ 424/245
4,208,411  6/1980  Ikura et al. ................ 424/245

Primary Examiner—Robert W. Ramsuer
Attorney, Agent, or Firm—Larson and Taylor

[57] ABSTRACT

A new imidazole compound is now provided, which is represented by the general formula

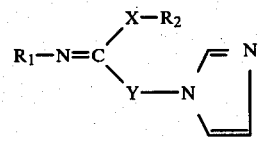

wherein
$R_1$ is naphthyl group, an arylalkyl group, a cycloalkyl group, a cycloalkylalkyl group, an alkyl group, a lower alkenyl group, a lower alkoxy-lower alkyl group or a phenylthio-lower alkyl group or phenyl group or a substituted phenyl group;
$R_2$ is an unsubstituted or substituted alkyl group or an alkenyl group or an alkynyl group, naphthyl group, or an unsubstituted or substituted phenyl group;
X is an oxygen atom or a sulfur atom; and
Y is an unsubstituted or substituted alkylene group or an unsubstituted or substituted alkenylene group. The new imidazole compound and its salt show a usefully high fungicidal activity against a wide variety of fungi which infest crop plants. The new imidazole compound and its salt may be useful as fungicidal agent of agricultural and horticultural usages.

9 Claims, No Drawings

IMIDAZOLE DERIVATIVES AND FUNGICIDAL COMPOSITION CONTAINING THE SAME

BACKGROUND OF THE INVENTION

1. Field of the Invention

This invention relates to new imidazole derivatives and their salts which exhibit a high fungicidal activity against a wide variety of fungi which usually infest crop plants in the agricultural field. This invention also relates to the use of these new imidazole derivatives or their salts as fungicidal agent of agricultural and horticultural utilities.

2. Description of the Prior Art

Many kinds of fungicidal compounds are known, and among of them, some imidazole derivatives are known to have the fungicidal activity. For instance, from Japanese patent application unexamined prepublication "Kokai" Sho 52-27767 (published on 2nd March, 1977, corresponding to U.K. patent applications No. 35208/75, No. 37241/75, No. 37244/75, No. 51039/75, No. 671/76 and No. 27649/76), it is known that an ester or an amide (including anilide) of an imidazol-1-yl-alkanoic acid represented by the general formula

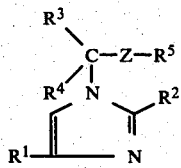

wherein $R^1$ and $R^2$ are each a hydrogen atom, a halogen atom, nitro or an alkyl group; $R^3$ and $R^4$ are each a hydrogen atom or a substituted or unsubstituted hydrocarbyl group; and $R^5$ is a hydroxyl group, a substituted or unsubstituted hydrocarbyloxy group, or an amino group, or a substituted or unsubstituted hydrocarbyl group other than a substituted or unsubstituted phenyl; and Z is a group $>C=O$ or $>C=S$ or a derivative of the group $>C=O$ is useful as fungicidal agent of agricultural and horticultural utilities. However, these known imidazole derivatives have not always satisfactorily high fungicidal activity against a wide variety of the fungal pests.

SUMMARY OF THE INVENTION

An object of this invention is to provide a new imidazole derivative which exhibits a satisfactorily high fungicidal activity against a wide variety of the fungal pests infesting the crop plants. A further object of this invention is to provide a new imidazole derivative which is of a low toxicity and usable with safety and is useful as a broad-spectrum fungicide. Another objects of this invention will be clear from the following descriptions.

We, the present inventors, have synthetized a number of new imidazole derivatives, and we have now found that a particular class of the new imidazole derivatives now synthetized which is represented by the general formula [I] shown hereinafter has a satisfactorily high fungicidal activity against a wide variety of fungi and exhibits a high preventive effect as well as a high curative effect for treatment of the fungal infections of crop plants. Besides, the new imidazole derivative of the general formula [I] has neither any objectionable phytotoxicity to crop plants, nor any objectionable toxicity to mammalian animals and fishes. It has been found that the new imidazole derivative of the general formula [I] and a salt thereof with an acceptable, inorganic or organic acid, as well as a complex salt thereof with a metal salt have very excellent properties as fungicidal agent of agricultural and horticultural utilities.

According to a first aspect of this invention, therefore, there is provided as the new compound an imidazole derivative of the general formula

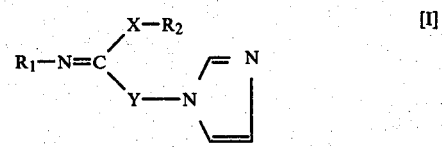

wherein
$R_1$ is naphthyl group, an arylalkyl group, a cycloalkyl group, a cycloalkylalkyl group, an alkyl group, a lower alkenyl group, a lower alkoxy-lower alkyl group, a phenylthio-lower alkyl group or phenyl group; the phenyl group being unsubstituted or substituted with 1 to 5 substituents which is or are the same or different from each other and selected from a halogen atom, nitro group, cyano group, a lower alkyl group, a lower alkenyl group, a halogenated lower alkyl group, a lower alkoxyl group, a lower alkenyloxy group, a lower alkylthio group, a lower alkylsulfinyl group, a lower alkylsulfonyl group, a lower alkylcarbonyl group, phenyl group, phenoxy group, a halogen-substituted phenoxy group, phenylthio group, a lower alkyl-substituted phenylthio group and a nitro-substituted phenylthio group;

$R_2$ is a saturated alkyl group, an unsaturated alkyl group, a lower alkoxy-lower alkyl group, a lower alkylthio-lower alkyl group, a phenoxy-lower alkyl group, a phenylthio-lower alkyl group, a mono- or di-lower alkylamino-lower alkyl group, a lower alkyl group substituted with a group $-N(CH_2)_n$ where n is an integer of 2 to 6, a lower alkylcarbonyl group, phenylcarbonyl group, a cycloalkyl group, a cycloalkylalkyl group, a halogenated lower alkyl group, a cyano-lower alkyl group, a lower alkoxycarbonyl-lower alkyl group, a lower alkylthiocarbonyl-lower alkyl group, an arylalkyl group, a lower alkylcarbonyl-lower alkyl group, a phenylcarbonyl-lower alkyl group, naphthyl group, furfuryl group or phenyl group; the latter phenyl group being unsubstituted or substituted with a substituent which is selected from a halogen atom, nitro group, cyano group and a lower alkyl group;

X is an oxygen atom or a sulfur atom; and
Y is a straight or branched saturated alkylene group or unsaturated alkylene group, the saturated alkylene group being unsubstituted or substituted with a halogen group, a lower alkoxyl group, cyano group, phenyl group, a halogen-substituted phenyl group, a nitro-substituted phenyl group, a lower alkyl-substituted phenyl group and/or trifluoromethyl-substituted phenyl group, or a salt of said imidazole derivative.

The imidazole compound of the general formula [I] may be termed as an O-ether of imidazole-1-yl-isothioacetic acid anilide or an S-ether of imidazole-1-yl-isothioacetic acid anilide or a derivative thereof and may also be termed as an N-substituted α-(imidazol-1-yl-alkyl)- or α-(imidazol-1-yl-alkenyl)-imino-acid ester or an N-substituted α-(imidazol-1-yl-alkyl)- or α-(imidazol-1-yl-alkenyl)-thio-imino-acid ester or a derviative thereof.

The term "lower alkyl" means an alkyl containing 1 to 6 carbon atoms. Similarly, the term "lower" attached to "alkenyl" or "alkoxy" group indicates that the alkenyl or alkoxy group is containing 1 to 6 carbon atoms.

According to a first preferred embodiment of the first aspect invention, there is provided as the new compound an imidazole derivative which is of the formula

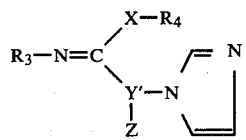

wherein

R₃ is naphthyl group, a phenyl-(C₁-C₄)alkyl group, a dichlorophenyl-(C₁-C₄)alkyl group, a (C₅-C₆)cycloalkyl group, a (C₅-C₆)cycloalkyl-(C₁-C₄)alkyl group, a (C₁-C₁₀)alkyl group, a (C₂-C₄)alkenyl group, a (C₁-C₄)alkoxy(C₁-C₄)alkyl group, a phenylthio-(C₁-C₄)alkyl group, phenyl group, a chlorophenyl group, a fluorophenyl group, a bromophenyl group, a nitrophenyl group, a cyanophenyl group, a trifluoromethylphenyl group, a dichlorophenyl group, a dibromophenyl group, a difluorophenyl group, a bromochlorophenyl group, a chlorofluorophenyl group, a trifluoromethylchlorophenyl group, a trichlorophenyl group, a dichloro-dimethylphenyl group, a trichlorodimethylphenyl group, a chloro-methoxyphenyl group, a chloro-methylphenyl group, a (C₁-C₄)alkylphenyl group, a di-(C₁-C₄)alkylphenyl group, a (C₂-C₄)alkenylphenyl group, a (C₂-C₄)alkenyloxyphenyl group, a (C₁-C₄)alkoxyphenyl group, a di-(C₁-C₄)alkoxyphenyl group, a (C₁-C₄)alkylthiophenyl group, a (C₁-C₄)alkylsulfinylphenyl group, a (C₁-C₄)alkylsulfonylphenyl group, a (C₁-C₄)alkylcarbonylphenyl group, diphenyl group, a phenoxyphenyl group, a chlorophenoxyphenyl group, a phenylthiophenyl group, a (C₁-C₄)alkylphenylthiophenyl group or a nitrophenylthiophenyl group, R₄ is a (C₁-C₁₀)alkyl group, a (C₂-C₄)alkenyl group, a (C₂-C₄)alkynyl group, a (C₁-C₄)alkoxy-(C₁-C₄)alkyl group, a (C₅-C₆)cycloalkyl-(C₁-C₄)alkyl group, a (C₁-C₄)-alkylthio(C₁-C₄)alkyl group, a phenyl-(C₁-C₄)alkyl group, a phenoxy(C₁-C₄)alkyl group, a dichlorophenoxy-(C₁-C₄)alkyl group, a phenylthio-(C₁-C₄)alkyl group, a (C₁-C₄)alkylamino(C₁-C₄)alkyl group, a di-(C₁-C₄)alkylamino-(C₁-C₄)alkyl group, a pyrrolyl-(C₁-C₄)alkyl group, a chloro-(C₁-C₄)alkyl group, a cyano-(C₁-C₄)alkyl group, a (C₁-C₄)alkoxycarbonyl(C₁-C₄)alkyl group, a (C₁-C₄)alkylthiocarbonyl-(C₁-C₄)alkyl group, a (C₁-C₄)alkylcarbonyl-(C₁-C₄)alkyl group, a phenylcarbonyl-(C₁-C₄)alkyl group, a (C₅-C₆)cycloalkyl group, benzyl group, a chlorobenzyl group, a dichlorobenzyl group, a fluorobenzyl group, a methylbenzyl group, a dimethylbenzyl group, a methylbenzylethyl group, naphthyl group, furfuryl group, phenyl group, a chlorophenyl group, a dichlorophenyl group, a cyanophenyl group, a nitrophenyl group, a (C₁-C₄)alkylphenyl group, a (C₁-C₄)alkylcarbonyl group, or benzoyl group, X is an oxygen atom or a sulfur atom;

Y' is a (C₁-C₄)alkylene group or a (C₂-C₄)alkenylene group; and

Z is a hydrogen atom, a (C₁-C₆)alkyl group, a (C₁-C₄)alkoxy-(C₁-C₄)alkyl group, a cyano-(C₁-C₄)alkyl group, a (C₂-C₄)alkenyl group, phenyl group, a chlorophenyl group, a dichlorophenyl group, a methylphenyl group, a trifluoromethylphenyl group, a nitrophenyl group, benzyl group, a chlorobenzyl group or a dichlorobenzyl group; or a salt of said imidazole derivative.

According to a second preferred embodiment of the first aspect invention, there is provided as the new compound an imidazole derivative which is of the formula

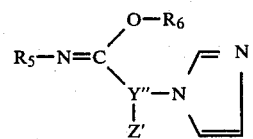 [Ib]

wherein

R₅ is phenyl group, a chlorophenyl group, a bromophenyl group, a nitrophenyl group, a trifluoromethylphenyl group, a dichlorophenyl group, a bromochlorophenyl group, a chlorofluorophenyl group, a trifluoromethylchlorophenyl group, a trichlorophenyl group, a dichlorodimethylphenyl group, a trichloro-dimethylphenyl group, a chloromethoxyphenyl group, a chloro-methylphenyl group, a (C₁-C₄)alkylphenyl group, a di-(C₁-C₄)alkylphenyl group, a (C₂-C₄)alkenyloxyphenyl group, a (C₁-C₄)alkoxyphenyl group, a di-(C₁-C₄)alkoxyphenyl group, a methylsulfonylphenyl group, an acetylphenyl group, a phenoxyphenyl group, or a nitrophenylthiophenyl group;

R₆ is a (C₁-C₁₀)alkyl group, a (C₂-C₄)alkenyl group, a (C₁-C₄)alkoxy-(C₁-C₄)alkyl group, a methylthio-(C₁-C₄)alkyl group, a dichlorophenoxy-(C₁-C₄)alkyl group, a phenylthio-(C₁-C₄)alkyl group, cyclohexyl group, an ethoxycarbonyl-(C₁-C₄)alkyl group, benzyl group, a chlorobenzyl group, a dichlorobenzyl group, naphthyl group, furfuryl group, phenyl group, a chlorophenyl group, a dichlorophenyl group, a cyanophenyl group, a nitrophenyl group, or a (C₁-C₄)alkylphenyl group, Y" is a linear (C₂-C₄)alkylene group, Z' is a hydrogen atom, a (C₁-C₆)alkyl group, a (C₂-C₄)alkenyl group, phenyl group, a chlorophenyl group, a dichlorophenyl group, a methylphenyl group, a nitrophenyl group, or benzyl group, or a salt of said imidazole derivative.

According to a third preferred embodiment of the first aspect of this invention, there is provided as the new compound an imidazole derivative which is of the formula

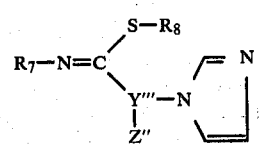 [Ic]

wherein
- R₇ is phenyl group, a chlorophenyl group, a fluorophenyl group, a bromophenyl group, or a nitrophenyl group, a cyanophenyl group, a trifluoromethylphenyl group, a dichlorophenyl group, a dibromophenyl group, a bromochlorophenyl group, a chlorofluorophenyl group, a trifluoromethylchlorophenyl group, a trichlorophenyl group, a dichloro-dimethylphenyl group, a trichloro-dimethylphenyl group, a chloro-methoxyphenyl group, a chloro-methylphenyl group, a ($C_1$–$C_4$)alkylphenyl group, a di-($C_1$–$C_4$)alkylphenyl group, a ($C_2$–$C_4$)alkenyphenyl group, a ($C_1$–$C_4$)alkoxyphenyl group, a di-($C_1$–$C_4$)alkoxyphenyl group, a methylthiophenyl group, a methylsulfinylphenyl group, a methylsulfonylphenyl group, an acetylphenyl group, diphenyl group, a phenoxyphenyl group, a chlorophenoxyphenyl group, a phenylthiophenyl group or a methylphenylthiophenyl group;
- R₈ is a ($C_1$–$C_{10}$)alkyl group, a ($C_2$–$C_4$)alkenyl group, a ($C_2$–$C_4$)alkynyl group, a ($C_1$–$C_4$)alkoxy-($C_1$–$C_4$)alkyl group, a methylthio-($C_1$–$C_4$)alkyl group, a phenoxy-($C_1$–$C_4$)alkyl group, a phenylthio-($C_1$–$C_4$)alkyl group, a ($C_1$–$C_4$)alkylamino-($C_1$–$C_4$)alkyl group, a pyrrolyl-($C_1$–$C_4$)alkyl group, a ($C_1$–$C_4$)alkylcarbonyl group, a ($C_5$–$C_6$)cycloalkyl group, a chloro($C_1$–$C_4$)alkyl group, a cyano-($C_1$–$C_4$)alkyl group, a ($C_1$–$C_4$)alkylthiocarbonyl-($C_1$–$C_4$)alkyl group, benzyl group, a chlorobenzyl group, a fluorobenzyl group, a dichlorobenzyl group, a methylbenzyl group, a methylbenzylethyl group, an acetyl-($C_1$–$C_4$)alkyl group, benzoyl group, a phenylcarbonyl-($C_1$–$C_4$)alkyl group or phenyl group;
- Y''' is a linear ($C_1$–$C_4$)alkylene group or a linear ($C_2$–$C_4$)alkenylene group; and
- Z'' is a hydrogen atom, a ($C_1$–$C_6$)alkyl group, a ($C_1$–$C_4$)alkoxy-($C_1$–$C_4$)alkyl group, a cyano-($C_1$–$C_4$)alkyl, a ($C_2$–$C_4$)alkenyl, phenyl group, a chlorophenyl group, a dichlorophenyl group, a methylphenyl group, benzyl group, a chlorobenzyl group or a dichlorobenzyl group; or a salt of the said imidazole derivative.

According to the third preferred embodiment of the first aspect invention, it is especially preferred that the new compound of this invention is of the formula [Ic] where R₇ is 2,4-dichlorophenyl, 2-trifluoromethyl-4-chlorophenyl or 2-chloro-4-fluorophenyl; R₈ is ethyl, benzyl or p-chlorobenzyl; Y''' is methylene; and Z'' is hydrogen, methyl or ethyl.

According to a fourth preferred embodiment of the first aspect invention, there is provided as the new compound an imidazole derivative which is of the formula

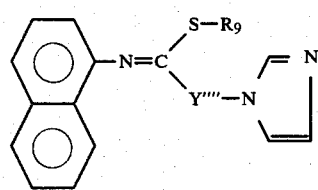

[Id]

wherein
- R₉ is a ($C_1$–$C_4$)alkyl group, a phenyl-($C_1$–$C_4$)alkyl group or a chloro-($C_1$–$C_4$)alkyl group; and Y'''' is a linear or branched ($C_1$–$C_4$)alkylene group, or a salt of the said imidazole derivative.

According to a fifth preferred embodiment of the first aspect invention, there is provided as the new compound an imidazole derivative which is of the formula

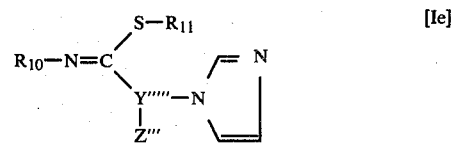

[Ie]

wherein
- R₁₀ is a ($C_5$–$C_6$)cycloalkyl group or a ($C_1$–$C_4$)alkyl group which is unsubstituted or substituted with phenyl group, a dichlorophenyl group, a ($C_2$–$C_4$)alkenyl group, a ($C_1$–$C_4$)alkoxy group or phenylthio group;
- R₁₁ is a ($C_1$–$C_4$)alkyl group which is unsubstituted or substituted with phenyl group, a di-($C_1$–$C_4$)alkylamino group, furanyl group or a ($C_5$–$C_6$)cycloalkyl group;
- Y''''' is a ($C_1$–$C_4$)alkylene group; and
- Z''' is a hydrogen atom, a ($C_1$–$C_6$)alkyl group, a chlorobenzyl group or a trifluoromethylphenyl group; or a salt of said imidazole derivative.

Particular examples of the new imidazole compounds according to the general formula [I] or the formula [Ia], [Ib], [Ic], [Id] or [Ie] are listed in Table 1 given hereinafter.

The new imidazole compound of this invention is belonging to a derivative of isoamides or isothioamides and is not described in any chemical literatures. The new imidazole compound of this invention is superior to the previously known fungicidal imidazole compounds in respect of the fungicidal activity to fungi of the fungal infections of crop plants. Thus, the new compound of this invention exhibits a wide ranged antifungal spectrum and is effective for treatment of a wide variety of fungal diseases of plants. In particularly, the compound of this invention is effective to control fungal diseases of cereals such as leaf rust (*Puccinia recondita*), stripe rust (*Puccinia striformus*), stem rust (*Puccinia graminis*) or dwarf leaf rust (*Puccinia hordei*) in wheat or barley; powdery mildew (*Erysiphe graminis*) in wheat and barley, leaf spot (*Helminthosporium maydis*) in rice, brown spot (*Cochliobolus setariae*) in corn; fungal diseases of beans such as rust (*Phakosora pachyrhizi*) in soybean; rust (*Uromyces fabae*) in broad bean, and anthracnose (*Collectotrichum lindemthianum*) in kidney-bean; as well as fungal diseases of vegetables such as powdery mildew (*Sphaerotheca fuliginea*) in cucumber, powdery mildew (*Sphaerotheca fuliginea*) in water melon, powdery mildew (*Erysiphe cichoracearum*) in egg plant and powdery mildew (*Leveillula taurica*) in sweet pepper; fungal diseases of cucurbitaceae such as anthracnose (*Collectotrichum lagenarium*) in cucumber, anthracnose (*Colletotrichum lagenarium*) in water melon, and anthracnose in sweet melon, and rust (*Puccinia allii*) in onion or stone-leek. The new compound of this invention is also effective even at a low rate of application to control fungal diseases of fruit-plants such as rust (*Gymnosporangium yamadae*), scaf (*Venturia inaequalis*) in apple, powdery mildew (*Podosphaera leucotricha*) in apple, rust (*Gymnosporangium haraeanum*), scab (*Venturia mashicola*) in pear, or rip rot (*Glomerella cingulata*) in grape. When the compound of this invention is used as seed disinfectant, it is highly effective to prevent browh spot and bakanae disease (*Gibberella fujikuroi*) on rice, and smuts (*Urocystis tritici* or *Ustilago hordei*) on barley and wheat, and barely bunt (*Tilletia pancicii*) on barley or wheat bunt (*Tilletia canie*) on wheat, and others.

The compound of this invention is much more effective for preventative treatment of the fungal diseases of plants and also much more effective for curative (protective) of the fungal diseases, as compared to the previously known fungicidal imidazole compounds. Amongst the fungicidal compounds which have been used as the antifungal agent for treatment of fungal diseases of plants in practice, only a few of them is known to exert the curative effects to a satisfactory extend in fields, and much less fewer compounds are known to exert highly favorable results both in the preventative treatment and in the curative treatment of the fungal diseases of plants. Although the compound of this invention shows a high fungicidal activity, it has no or little phyto-toxicity to the useful plants and has not any objectionable toxicity to men and animals and also to fishes. Accordingly, the compound of this invention can be utilized with safety. Thus, the compound of this invention is highly safe as the fungicidal agent of agricultural and horticultural utilities and besides it is highly effective not only in the preventative treatment but also in the curative treatment of the various, fungal diseases of plants, so that the compound of this invention is greatly promising in the fields of agriculture and horticulture.

The imidazole compound of the formula [I] according to this invention can be produced, for example, by three different processes which are shown by the reaction equations (a), (b) and (c) given below, respectively.

In accordance with the first process, the imidazole compound of the formula [I] is produced by reacting an N-substituted α-(imidazol-1-yl)alkyl- or α-(imidazol-1-yl)alkenyl-imino (or thio-imino)-acid halide or a reactive equivalent thereof having the formula [II] given below, with an alcohol or a mercaptan having the formula [III] given below, according to the following reaction equation (a):

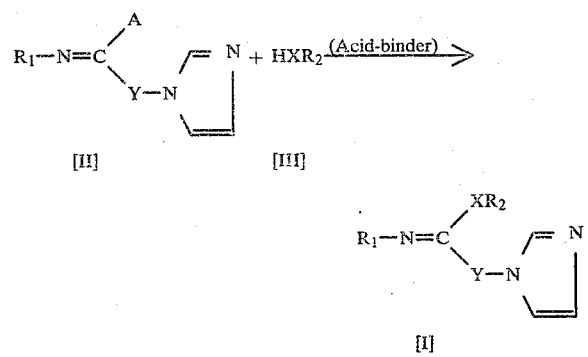

wherein $R_1$ and Y appearing in the formula [II] have the same meanings as defined in the formula [I] and A is a halogen atom such as chlorine or bromine, imidazol-1-yl group, an alkylsulfonyl group such as mesyl or an arylsulfonyl group such as tosyl group and wherein X and $R_2$ in the formula [III] have the same meanings as defined in the formula [I].

The starting compound of the general formula [II] is containing the imidazole group like to the imidazole compound of the general formula [I] and hence may be provided also in the form of a salt thereof with an inorganic acid or organic acid or in the form of a metal salt complex. The reactant compound of the general formula [III] contains the groups X and $R_2$ which are the same as those present in the final product compound of the formula [I], respectively. The reactant compound [III] belongs to the class of alcohols or mercaptans and may readily be prepared by known chemical methods.

In carrying out the reaction of the compound [II] with the compound [III] according to the reaction equation (a), any solvent serving as the reaction medium may not always be used, though usually an organic solvent may preferably be used. In some cases, an excess of the compound [III] may be used as the solvent. The organic solvent available for this purpose includes hydrocarbons, halogenated hydrocarbons, ethers, ketones, nitriles, acidamides, dimethylsulfoxide and the like. If necessary, it is possible to provide the presence of an amount of an acid-binder which will bind the hydrogen halide as liberated during the reaction. However, the use of the acid-binder is not always required, as both the compound [II] and the compound [I] themselves are basic compounds. The acid-binder as used may be an organic amine such as triethylamine and pyridine or may be an inorganic base such as potassium carbonate and the like. The compound of the formula [III] may be provided in the form of its sodium or potassium salt (alcoholate or mercaptide) which has previously been prepared by reacting it with metallic sodium, metallic potassium, sodium amide or sodium hydride. The reaction may proceed at ambient temperature but may be promoted at an elevated temperature to be completed in a shorter reaction time. When the acid-binder is used, the reaction solution may be filtered after completion of the reaction, so that the salt of the acid-binder deposited in the reaction solution is removed. The resultant filtrate is distilled to remove the solvent for recovery of the compound of the invention. Alternatively, the reaction solution may be admixed with a volume of a water-immiscible organic solvent such as benzene, chloroform, ethylether or tetrahydrofuran and also with a volume of water and the admixture obtained is stirred, followed by separation of the organic phase from the aqueous phase and by removal of the organic solvent from the organic phase by distillation to afford the compound of the invention. The first process of producing the compound of this invention according to the reaction equation (a) is illustrated with reference to Examples 1-6 given later.

In accordance with the second process, the imidazole compound of the formula [I] may be produced by reacting an N-substituted imino-ether or thioimine-ether of the formula [IV] given below, with imidazole of the formula [V] according to the following reaction equation (b):

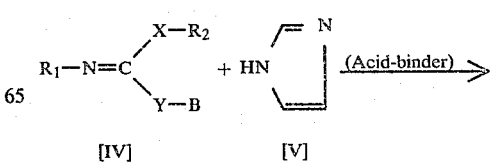

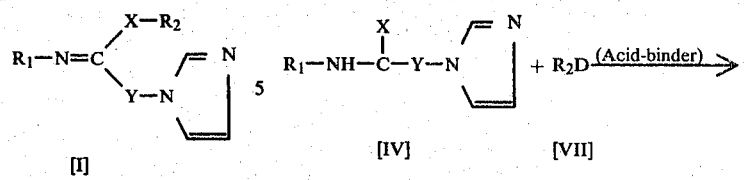

[I]

wherein $R_1$, X, $R_2$ and Y appearing in the formula [IV] are as defined hereinbefore and B is a halogen atom such as chlorine or bromine, an alkylsulfonyl group such as mesyl or an arylsulfonyl group such as tosyl, or benzenesulfonyl. The compound of the formula [V], namely imidazole is morphoteric and may be provided either as a salt of the anion-form of imidazole with an alkali metal cation, or as a salt of the cation-form of imidazole with an inorganic or organic acid or as a salt complex of the cation-form of imidazole with a metal salt.

In carrying out the reaction of the compound [IV] with the compound [V] according to the reaction equation (b), any solvent serving as the reaction medium is not necessary to be used, but usually an organic solvent may preferably be used as the reaction medium. In some cases, an excess of the compound of the formula [V] may be present as the reaction medium solvent. The organic solvent available for this purpose includes hydrocarbons, halogenated hydrocarbons, ethers, esters, ketones, nitriles, alcohols, acid amides, dimethylsulfoxide and the like. The presence of a polar organic solvent is useful to reduce the required reaction time. As the compound [V] is basic, it is not necessary to provide the presence of an additional acid-binder in the reaction mixture. If desired, however, it is possible to use an organic amine such as triethylamine and pyridine or an inorganic base such as potassium carbonate as the acid-binder. The compound of the formula [V] may be provided in the form of its salt which has previously been prepared by reacting it with metallic sodium, metallic potassium, sodium amide or sodium hydride. The reaction may proceed at ambient temperature but a required reaction time may be reduced by warming the reaction mixture.

When the acid-binder is used in the reaction (b), the reaction solution is filtered after completion of the reaction to remove the salt of the acid-binder as formed during the reaction. The filtrate is distilled to remove the organic solvent and the compound of this invention is recovered. Alternatively, the reaction solution may be admixed with a volume of a water-immiscible organic solvent such as benzene, chloroform, ethylether or tetrahydrofuran and also with a volume of water, and the whole admixture is stirred, followed by separation of the organic phase from the aqueous phase and further by removal of the organic solvent from the organic phase by distillation to afford the compound of the invention.

The second process of producing the compound of the invention according to the reaction equation (b) is illustrated by Examples 7 and 8 given later.

In accordance with the third process, the compound of the invention may be made by reacting an N-substituted amide compound of the formula [VI] given below, with a halide compound or a reactive equivalent thereof having the formula [VIII] given below, according to the following reaction equation (c):

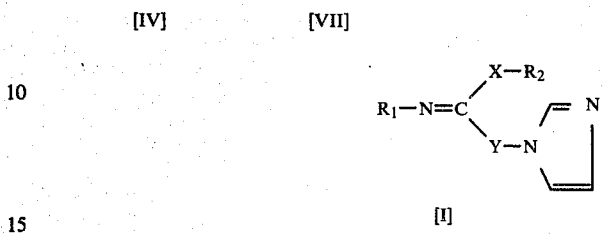

wherein $R_1$, X and Y appearing in the general formula [VI] are as defined hereinbefore. The starting compound of the formula [VI] contains the imidazolyl group and may be provided in the form of a salt with an inorganic or organic acid or in the form of a metal salt complex. In the reactant compound of the general formula [VII], the group $R_2$ has the same meaning as that present in the compound of the general formula [I], and the group D denotes a halogen atom such as chlorine or bromine, an alkylsulfonyl group such as mesyl or an arylsulfonyl group such as tosyl. The reactant compound [VII] may easily be prepared by known chemical processes. The process of producing the compound [I] according to the reaction equation (c) may be carried out with advantage, particularly when the starting compound [VI] contains a sulfur atom as a value of X. The reaction of the compound [VI] with the compound [VII] according to the reaction equation (c) may be conducted without any solvent as the reaction medium. Usually, however, an organic solvent may preferably be provided as the reaction medium. If desired, an excess of the compound [VII] may be utilized as the reaction medium solvent. The organic solvent available for this purpose includes hydrocarbons, halogenated hydrocarbons, ethers, esters, ketones, nitriles, alcohols, dimethylsulfoxide and the like. As the compound [VI] is basic, it is not necessary to provide the presence of an additional acid-binder in the reaction mixture. If desired, however, it is preferable to use an organic amine such as triethylamine and pyridine or an inorganic base such as potassium carbonate as the acid-binder. The compound of the formula [VI] may be provided in the form of its salt which has previously been prepared by reacting it with metallic sodium, metallic potassium, sodium amide or sodium hydride or an alkali metal alcoholate. The reaction may proceed at ambient temperature but a required reaction time may be reduced by warming the reaction mixture. When the acid-binder is used in the reaction (c), the reaction solution is filtered after completion of the reaction to remove the salt of the acid-binder as deposited during the reaction. The filtrate is distilled to remove the organic solvent and the compound of this invention is recovered. Alternatively, the reaction solution may be admixed with a volume of a water-immiscible organic solvent such as benzene, chloroform, ethylether or tetrahydrofuran and also with a volume of water, and the whole admixture is stirred, followed by separation of the organic phase from the aqueous phase and further by removal of the organic solvent from the organic phase by distillation to afford the compound of the invention.

The third process of producing the compound of the invention according to the reaction equation (c) is demonstrated by Example 9 shown later.

The imidazole compound of the formula [I] according to the invention may be in the form of its salt which includes a salt of the imidazole compound with an inorganic acid or a salt of the imidazole compound with an organic acid and a salt complex of the imidazole compound with a metal salt.

The inorganic acid suitable for the salt formation includes: hydrohalogenic acids such as hydrochloric, hydrobromic or hydroiodic acid; sulfuric acid, nitric acid, perchloric acid, phosphoric acid and sulfamic acid. The preparation of the salt of the imidazole compound with an inorganc acid may be achieved by dissolving or suspending the imidazole compound [I] in water or a suitable organic solvent and admixing the resultant solution or suspension with a stoichiometrical quantity of the acid which may be provided as such or may have been diluted with the organic solvent. If the acid used is gaseous, it may be blown into the solution or suspension of the imidazole compound. Generally, this salt-forming reaction may proceed rapidly at ambient temperature or even under cooling. When the inorganic acid salt formed is deposited as crystals, these may be separated by filtration. In some cases, the salt-forming reaction solution may be distilled to remove the solvent therefrom, affording the compound of this invention in the salt form. The preparation of the inorganic acid salt of the compound of this invention is illustrated by Examples 10–12.

The organic acid suitable for the salt formation includes: a saturated or unsaturated aliphatic acid, either substituted or unsubstituted; an arylcarboxylic acid such as benzoic acid; an alkyl- or aryl-sulfonic acid; a mono- or di-substituted alkyl- or aryl-sulfonic acid; and esters and amides of phosphoric acid or phosphonic acid, including their sulfur homologues. Particular examples of the suitable acids for this purpose may be, for example, formic acid, acetic acid, acrylic acid, monochloroacetic acid, dichloroacetic acid, trichloroacetic acid, cyanoacetic acid, oxalic acid, malonic acid, maleic acid, fumaric acid, succinic acid, malonic acid, glyoxalic acid, pyruvic acid, benzoic acid, p-nitrobenzoic acid, 2,4,6-trinitrobenzoic acid, methanesulfonic acid, octylsulfonic acid, benzenesulfonic acid, toluenesulfonic acid, dimethylsulfamic acid, cyclohexylsulfamic acid, phenylsulfamic acid, O,O-diethylphosphoric acid, O,O-diethylmonothiophosphoric acid, O,O-diethyldithiophosphoric acid, O-ethyl-phenylphosphonic acid, O-ethylphosphoric acid or phenylphosphonic acid. The formation of the salt of the imidazole compound with an organic acid may be achieved by dissolving or suspending the compound [I] in water or a suitable organic solvent and admixing the resultant solution or suspension with a stoichiometric quantity of the organic acid which may optionally have been diluted with water or with the organic solvent. The salt-forming reaction may proceed at ambient temperature or even under cooling. The reaction mixture may be heated, if necessary. When the organic acid salt of the imidazole compound as formed is deposited as crystals, these may be separated by filtration. In some cases, the compound of the invention in the salt form may be recovered by removing the solvent from the salt-forming reaction solution by distillation. The preparation of the organic acid salt of the imidazole compound of the invention is illustrated by Examples 13–15.

The cation present in the metal salt suitable for the formation of the complex salt of the imidazole compound [I] includes: metal cations such as copper, manganese, zinc, cobalt, nickel, iron, aluminum, silver, magnesium, tin, calcium and the like. The anion present in such metal salt includes an inorganic anion such as chlorine, bromine, iodine, fluorine anion; sulfuric, nitric or phosphoric acid anion; as well as an organic anion such as formic, acetic, methanesulfonic or toluenesulfonic acid anion and the like. The formation of the complex salt of the imidazole compound [I] with a metal salt may be achieved usually by reacting the compound [I] with a metal salt in water or an inert organic solvent. The inert organic solvent available for this purpose may be methanol, acetonitrile, dioxane, ethyl ether, dichloromethane, chloroform or hexane. The compound [I] and the metal salt reactant may properly be reacted with each other in a stoichiometrical or substantially stoichiometric molar proportion. When some metal cation is ued for formation of the complex salt, there are formed two complexes of which the ligands are different from each other. The complex-forming reaction usually can proceed at ambient temperature without the necessity of heating the reaction mixture. If the complex salt of the imidazole compound with the metal salt is deposited as crystals, the latter may be recovered by filtration to afford the compound of the invention in the complex form. In some cases, the complex-forming reaction solution may be distilled to remove the solvent therefrom, yielding the complex form of the compound of the invention. The preparation of the metal salt complex is demonstrated by Examples 16–20 shown later.

The imidazole compound of the invention may be used as such for anti-fungal agent but more conveniently formulated into compositions for such antifungal purposes.

This invention therefore provides a fungicidal composition comprising, as an acctive ingredient, an imidazole compound of the general formula [I] or a salt thereof, in association with an acceptable carrier for the active ingredient.

The invention further provides a method of combating the fungal pests of plants, which comprises treating plants, seeds or trees with an imidazole compound of the formula [I] or a salt thereof as hereinbefore described.

The compound of the invention can be used to combat the fungal pests of plants or seeds in a number of ways, and for example, the compound of the invention as such or in the form of a formulation can be applied directly to the foliage of a plant which is infected or likely to become infected, or they can be applied also to bushes and trees, to seeds or to other medium in which plants, bushes or trees are growing or are to be planted, or they can be sprayed on, dusted on or applied as a cream. Application can be made to any part of the plant, bush or tree, for example, to the foliage, stems, branches or roots, or to soil surrounding the roots.

The term "treating" as used means all these ways of application and the term "plant" includes seedlings, bushes and trees.

The compound of the invention are preferably used for agricultural and horticultural purposes in the form of a composition. The type of composition used in any instance will depend upon the particular purpose envisaged.

Generally, the composition of this invention may comprise any of the additive which are conventionally employed in the formulations of agricultural and horticultural usages, such as emulsifying agents, wetting agents, extending agents, dispersion agents and degradation-preventors, by which the effects of the composition as applied can be sured for the intended pesticidal purposes.

The composition of this inventin may be prepared by formulating the compound of the general formula [I] into the form of emulsifiable concentrate, wettable powder, sol (flowable powder), dusting powder, driftless (DL-type) powder, small granules or granules, etc., according to conventional formulation technique. The carrier material which may be admixed with the active compound of this invention may be any solid or liquid ones which have been used conventionally in the preparations for agricultural and horticultural usages. The liquid carrier available in the formulation of this invention includes various solvents, such as, water, aromatic hydrocarbons, aliphatic hydrocarbons, alcohols, esters, ketones, acid amides, dimethylsulfoxide and the like. The solid carrier includes mineral powders such as clay, talc, kaolin, bentonite, diatomaceous earth, calcium carbonate and silica and the like, as well as organic powders such as wood powder and others.

More particularly, the composition of this invention may be in the form of dusting powder in which the active compound is mixed with a solid carrier such as kaolin, bentonite, or it may be in the form of granules in which the active compound is absorbed in a porous granular material such as pumice.

The composition of this invention may also be in the form of liquid preparations to be used as dips or sprays, which are usually aqueous dispersion or emulsion of the active ingredient compound of this invention together with one or more of the known wetting agents, dispersing agents or emulsifying agents.

Wetting agents, dispersing agents and emulsifying agents may be of the cationic, anionic or non-ionic type. Suitable agents of the cationic type may be, for example, quaternary ammonium compounds, for example, cetyltrimethyl ammonium bromide. Suitable agents of the anionic type may be, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and the sodium salts of diisopropyl- or triisoproylnaphthalene sulphonates. Suitable agents of the non-ionic type may be, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters of long chain fatty acids and hexitol anhydrides and the condensation products of the said partial esters with ethylene oxide. The composition of the invention may contain a thickening agents such as gum, aliphatic acid salt, methylcellulose and the like.

The compositions to be used as sprays may also be in the form of aerosols wherein the formulation is charged in a container under pressure together with a propellant such as fluorotrichloromethane or dichlorodifluoromethane. The compositions to be used in the form of aqueous dispersions or emulsions are generally supplied in the form of a concentrate containing a high proportion of the active ingredient compound, and said concentrate may be diluted with water before use. These concentrates are often required to withstand storage for prolonged periods and after such storage, to be capable of dilution with water to form aqueous preparations which remain homogeneous for a sufficient time to enable them to be applied by conventional spray equipment.

The composition of this invention in the form of the concentrates such as wettable powder, liquid preparations and emulsifiable concentrate may contain the active compound of the invention in an amount of 1 to 95% by weight and usually of 2 to 75% by weight based on the whole weight of the composition. These preparations may be diluted with water upon use to give an aqueous preparation containing 0.0001 to 10% by weight of the active compound. The powders and granules may contain 0.1 to 10% by weight of the active compound. Such concentrates as oily solution or disperson, emulsifiable concentrates and sol (flowable powder) may directly be applied as the spraying formulation at a minimized rate of application, without being diluted with water before use. The wettable powder or other powders may be used as such as the seed-dressing agent to over coat the seeds of crop plants. The seeds may also be dipped in the liquid formulation is prepared by diluting the wettable powder, sol or emulsifiable concentrate with water.

When the compound of this invention is used as the fungicidal agent of agricultural and horticultural utilities, it may be applied in admixture with insecticides, another fungicides, bactericides, herbicides, plant-growth regulators and others, for broadening the range of applicability that the compound of this invention can be used effectively for the intended pesticidal purposes. In some cases, synergism can be expected by the combined used of the compound of this invention with another pesticides.

Examples of fungicides and bactericides which may be used in admixture with the compounds of this invention include the following:

Carbamate fungicides such as 3,3'-ethylenebis(tetrahydro-4,6-dimethyl-2H-1,3,5-thiadiazine-2-thione), zinc or manganese ethylenebis(dithiocarbamate), bis(-dimethyldithiocarbamoyl)disulfide, zinc propylenebis(-dithiocarbamate), bis(dimethyldithiocarbamoyl)ethylenediamine; nickel dimethyldithiocarbamate, methyl 1-(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10,11-dehydrodibenzo (b,f)azepine; pyridine fungicides such as zinc bis(1-hydroxy-2(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6-diethylphenyl)phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1,4-oxathine-3-carboxanilido-4,4-dioxide and 5,6-dihydro-2-methyl-1,4-oxathine-3-carboxanilide; naphthoquinone fungicide such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-s-triazol(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1-2,4-thiadiazole; 2,4-dichloro-6-(O-chloroanilino)-1,3,5-triazine; 2,3-dicyano-1,4-dithioanthraquinone; copper 8-quinolinate, polyoxine; validamycin; cycloheximide; iron methanearsonate; diisopropyl-1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)-5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinimide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolo[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenylsulfamide; ethyl-N-(3-dimethylaminopropyl)thiocarbamate hydrochloride; piomycin; S,S-6-methylquinoxaline-2,3-diyldithiocarbonate; complex of zinc and manneb; di-zinc bis(dimethyldithiocarbamate) ethylenebis (dithiocarbamate).

Examples of plant growth regulators and herbicides which may be used in combination with the compounds of this invention includes the following: isourea plant growth regulators such as N-methoxycarbonyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; triazine herbicides such as 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-s-triazine and 2-methylthio-4-ethylamino-6-isopropylamino-s-triazine; phenoxy herbicides such as 2,4-dichlorophenoxyacetic acid and methyl, ethyl and butyl esters thereof, 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether, 2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate, S-ethyl-N-cyclohexyl-N-ethylthiolcarbamate and S-ethyl-hexahydro-1H-azepine-1-carbothioate and S-ethyl-N,N-di-n-propylthiocarbamate; pyridinium herbicides such as 1,1'-dimethyl-4,4'-bispyridinium dichloride; phosphoric herbicides such as N-(phosphonomethyl)glycine; aniline herbicides such as $\alpha,\alpha,\alpha$-trifluoro-2,6-dinitro-N,N-dipropyl-p-toluidine, 4-(methylsufonyl)-2,6-dinitro-N,N-dipropylaniline and $N^3, N^3$-diethyl-2,4-dinitro-6-trifluoromethyl-1,3-phenylene diamine; acid anilide herbicids such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4(2,4-dichlorobenzoyl)-5-hydroxypyrazole and 1,3-dimethyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl,N-(4-chlorophenyl)carbamoyl]-4-chloro-5-methyl-4-isooxazoline-3-one; 3-isopropylbenzo-2-thia-1,3-diazinone-(4)-2,4-dioxide and 3-(2-methylphenoxy)pyridazine.

Examples of insecticides which may be mixed with the compounds of this invention include the following: phosphoric insecticides such as O,O-diethyl O-(2-isopropyl-4-methyl-6-pyrimidinyl)phosphorothioate, O,O-dimethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)-phosphorodithioate, O,O-dimethyl S-(N-methyl-N-formylcarbamoylmethyl) phosphorodithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphophonate, O,O-diethyl-O-(5-phenyl-3-isooxazolyl)phosphorothioate, O,O-dimethyl O-(2,5-dichloro-4-bromophenyl)phosphorothioate, O,O-dimethyl O-(3-methyl-4-methylmercaptophenyl)thiophosphate, O-ethyl O-p-cyanophenyl phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl] O,O-diethyl phosphorodithioate, 2-chloro-1-(2,4-dichlorophenyl)vinyl diethylphosphate, O,O-diethyl O-(3-oxo-2-phenyl-2H-pyridazine-6-yl) phosphorothioate, O,O-dimethyl S-(1-methyl-2-ethylsulfinyl)-ethyl phophorothiolate, O,O-dimethyl S-phthalimidomethyl phosphorodithioate, O,O-diethyl S-(N-ethoxycarbonyl-N-methylcarbamoylmethyl)phosphorodithioate, O,O-dimethyl S-[2-methoxy-1,3,4-thiadiazol-5-(4H)-onyl-(4)-methyl] dithiophosphate, 2-methoxy-4H-1,3,2-benzooxaphosphorine 2-sulfide, O,O-diethyl O-(3,5,6-trichloro-2-pyridyl)phosphorothiate, O-ethyl O-2,4-dichlorophenyl thionobenzene phosphonate, S-[4,6-diamino-s-triazine-2-yl-methyl] O,O-dimethyl phosphorodithioate, O-ethyl O-p-nitrophenyl phenyl phosphorothioate, O,S-dimethyl N-acetyl phosphoroamidothioate, 2-diethylamino-6-methylpyrimidine-4-yl-diethylphosphorothionate, 2-diethylamino-6-methylpyrimidine-4-yl-dimethylphosphorothionate, O,O-diethyl O-N-(methylsulfinyl) phenyl phosphorothioate, O-ethyl S-propyl O-2,4-dichlorophenyl phosphorodithioate and cis-3-(dimethoxyphosphinoxy)N-methyl-cis-crotone amide; carbamate insecticides such as 1-naphthyl N-methylcarbamate, S-methyl N-[methylcarbamoyloxy]thioacetoimidate, m-tolyl methylcarbamate, 3,4-xylyl methylcarbamate, 3,5-xylyl methylcarbamate, 2-sec-butylphenyl N-methylcarbamate, 2,3-dihydro-2,2-dimethyl-7-benzofuranylmethylcarbamate, 2-isopropoxyphenyl N-methylcarbamate, 1,3-bis(carbamoylthio)-2-(N,N-dimethylamino)propane hydrochloride and 2-diethylamino-6-methylpyrimidine-4-yl-dimethyl-carbamate; and another insecticides such as N,N-dimethyl N'-(2-methyl-4-chlorophenyl)formamidine hydrochloride, nicotine sulfate, milbemycin, 6-methyl-2,3-quinoxalinedithiocyclic S,S-dithiocarbonate, 2,4-dinitro-6-sec-butylphenyl dimethylacrylate, 1,1-bis(p-chlorophenyl) 2,2,2-trichloroethanol, 2-(p-tert-butyl-phenoxy)isopropyl-2'-chloroethylsulfite, azoxybenzene, di-(p-chlorophenyl)-cyclopropyl carbinol, di[tri(2,2-dimethyl-2-phenylethyl)tin]oxide, 1-(4-chlorophenyl)-3-(2,6-difluorobenzoyl) urea and S-tricyclohexyltin O,O-diisopropylphosphorodithioate.

The compound of this invention may also be admixed with fertilisers such as nitrogen-containing fertiliser or phosphorous-containing fertiliser. The composition may comprises granules of fertiliser which have been coated with the compound of this invention or in which the compound of this invention has been incorporated.

This invention is now illustrated with reference to the following Examples. Examples 1 to 20 are illustrative of the production of the new compound of this invention. Examples 21 to 26 are illustrative of the formulations containing the compound of this invention. Examples 27 to 33 are illustrative of the tests of estimating the fungicidal activities of the compound of this invention.

EXAMPLE 1

Production of Compound No. 1 identified in Table 1 later and of the formula

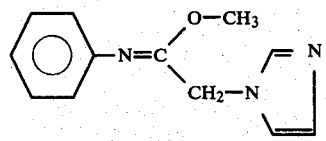

To a mixture of 25.6 g of the compound (imidazol-1-yl-acetic acid phenylimidoyl chloride hydrochloride) of the formula

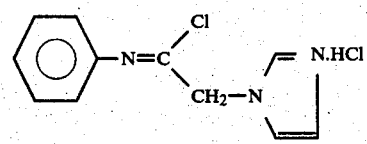

and 100 ml of methanol was added dropwise under ice-cooling a solution in methanol of sodium methoxide which was prepared by reacting 4.6 g of metallic sodium with 50 ml of methanol. The whole admixture obtained was stirred at ambient temperature for 30 minutes, and the salt deposited was removed from the reaction solution by sucking-filtration. The filtrate was concentrated under reduced pressure to give imidazol-1-yl-isoacetic acid anilide O-methylether (Compound No. 1) as a lightly yellow colored oil in a yield of 19.8 g. This substance was purified in silica gel column chromatography (developed with a mixed solvent of benzene and acetone) to give a pure product as a colorless oil which showed a refractive index $n_D^{23} = 1.5738$.

EXAMPLE 2

Production of Compound No. 102 of Table 1 and of the formula

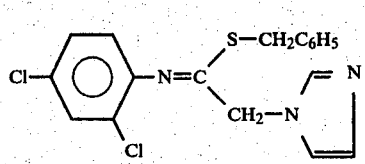

To a mixture of 32.5 g of the compound (imidazol-1-yl-acetic acid 2',4'-dichlorophenylimidoyl chloride hydrochloride) of the formula

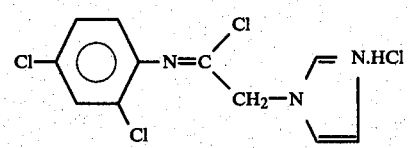

and 12.4 g of benzylmercaptan and 200 ml of acetonitrile was added dropwise 21.0 g of triethylamine (as the acid-binder) under ice-cooling. The whole admixture obtained was stirred at ambient temperature for 10 minutes, and the reaction solution was admixed with water and benzene. After stirring, the organic layer was separated and washed with 1 N aqueous sodium hydroxide and then with water, followed by drying over anhydrous sodium sulfate. The dried solution was distilled under reduced pressure to remove the solvent, and there was afforded imidazol-1-yl-isothioacetic acid 2',4'-dichloroanilide S-benzylether (Compound No. 102) as a lightly yellow colored oil in a yield of 31.6 g. This oil was purified in silica gel column chromatography to give a pure product as colorless oil which showed a refractive index $n_D^{23} = 1.6411$.

EXAMPLE 3

Production of Compound No. 115 of Table 1 and of the formula

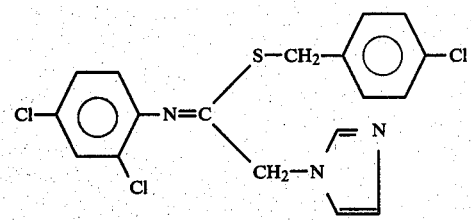

The compound (imidazol-1-yl-acetic acid 2',4'-dichlorophenylimidoyl imidazol) (32.0 g) of the formula

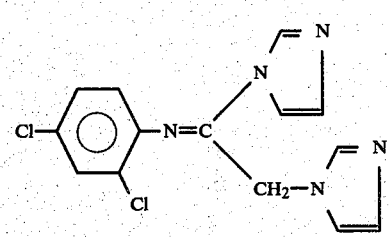

and p-chlorobenzylmercaptan (16.0 g) were dissolved in 150 ml of acetonitrile, and the resultant solution was reflexed for 30 minutes.

The reaction solution, after cooling, was admixed with water and benzene. After stirring, the organic layer was separated and washed with 1 N aqueous sodium hydroxide and then with water, followed by drying over anhydrous sodium sulfate. The dried solution was distilled under reduced pressure to remove the solvent, and there was afforded imidazol-1-yl-isothioacetic acid 2',4'-dichloroanilide S-p-chlorobenzylether (Compound No. 115) as lightly yellow colored crystals. Recrystallization from a mixed solvent of n-hexane/acetone gave the pure product as colorless crystals which showed a melting point of 94°–95° C.

EXAMPLE 4

Production of Compound No. 131 of Table 1 and of the formula

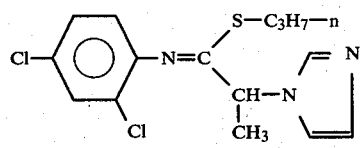

To a mixture of 30.3 g of α-imidazol-1-yl-propionic acid 2',4'-dichlorophenylimidoyl chloride of the formula

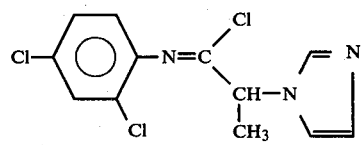

and 8.0 of n-propylmercaptan and 100 ml of acetone was added 14.0 g of anhydrous potassium carbonate (as the acid-binder). The whole admixture obtained was refluxed for one hour, and the reaction solution, after cooling, was admixed with water and benzene. After stirring, the organic layer was separated from the aqueous layer and washed with 1 N aqueous sodium hydroxide and then with water, followed by drying over anhydrous sodium sulfate. The dried solution was distilled under reduced pressure to remove the solvent, and there was afforded α-imidazol-1-yl-isothiopropionic acid 2',4'-dichloroanilide S-n-propylether (Compound No. 131) as a yellow colored oil in a yield of 31.1 g. This oil was purified in silica gel column chromatography to give a pure product as a lightly colored oil which showed a refractive index $n_D^{23} = 1.5928$.

EXAMPLE 5

Production of Compound No. 181 of Table 1 and of the formula

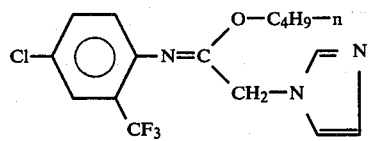

Imidazol-1-yl-acetic acid 4'-chloro-2'-trifluoromethylphenylimidoyl imidazole (35.4 g) of the formula

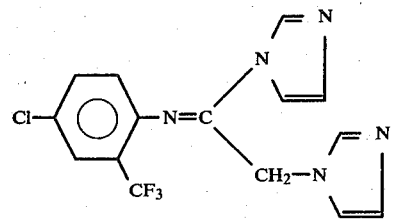

was dissolved in 100 ml of n-butanol, and the resultant solution was refluxed for 5 hours. The reaction solution was distilled under reduced pressure to remove n-butanol and then admixed with water and benzene. After stirring, the resultant organic layer was separated and washed with 1 N aqueous sodium hydroxide and then with water, followed by drying over anhydrous sodium sulfate. The dried solution was distilled under reduced pressure to remove the solvent, and there was afforded imidazol-1-yl-isoacetic acid 4'-chloro-2'-trifluoromethylanilide O-n-butylether (Compound No. 181) as a lightly colored oil in a yield of 29.5 g. This oil was purified in silica gel column chromatography to give a pure product as a colorless oil which showed a refractive index $n_D^{23} = 1.5900$.

EXAMPLE 6

Production of Compound No. 195 of Table 1 and of the formula

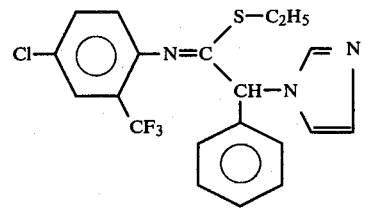

To a mixture of 39.8 g of α-imidazol-1-yl-phenylacetic acid 4'-chloro-2'-trifluoromethylphenylimidoyl chloride of the formula

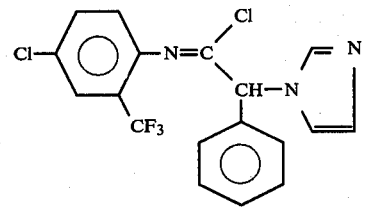

and 7.0 g of ethylmercaptan and 150 ml of acetonitrile was added dropwise 11.0 g of triethylamine (as the acid-binder). The whole admixture obtained was stirred at ambient temperature for one hour, and the reaction solution was admixed with water and benzene. After stirring, the resultant organic layer was separated and washed with 1 N aqueous sodium hydroxide and then with water, followed by drying over anhydrous sodium sulfate. The dried solution was distilled under reduced pressure to remove the solvent, and there was afforded α-imidazol-1-yl-isothiophenylacetic acid 4'-chloro-2'-trifluoromethylanilide S-ethylether (Compound No. 195) as a yellow colored oil in a yield of 39.0 g. This oil was purified in silica gel column chromatography to give a pure product as a lightly colored oil which showed a refractive index $n_D^{23} = 1.5946$.

EXAMPLE 7

Production of Compound No. 85 of Table 1 and of the formula

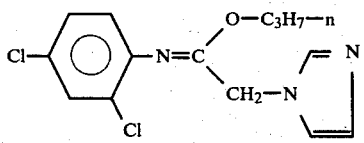

6.8 g of imidazole was added to a solution in n-propanol of sodium n-propoxide which was prepared by reacting 2.3 g of metallic sodium with 200 ml of n-propanol, and the admixture obtained was refluxed for 30 minutes. The reaction solution, after cooling, was admixed with 28.1 g of chloroisoacetic acid 2',4'-dichloroanilide O-n-propylether of the formula

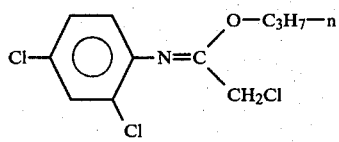

and the resultant admixture was refluxed for 2 hours. After cooling, the salt deposited was removed from the reaction solution by filtration under sucking, and the filtrate was concentrated under reduced pressure to give imidazol-1-yl-isoacetic acid 2',4'-dichloroanilide O-n-propylether (Compound No. 85) as a lightly colored oil in a yield of 29.0 g. This oil was purified in silica gel column chromatography to give a pure product as a colorless oil which showed a refractive index $n_D^{23} = 1.5686$.

EXAMPLE 8

Production of Compound No. 186 of Table 1 and of the formula

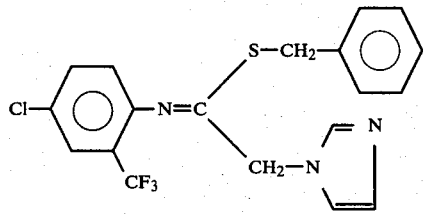

Chloroisothioacetic acid 4'-chloro-2'-trifluoromethylanilide S-benzylether (37.8 g) of the formula

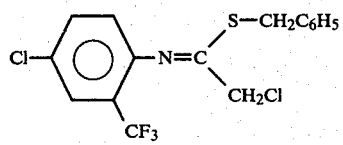

and imidazole (14.0 g) were dissolved in 100 ml of dimethylformamide, and the resultant solution was maintained at 100° C. for 2 hours for reaction. The reaction solution, after cooling, was admixed with water and benzene. After stirring, the resultant organic layer was separated and washed with 1 N aqueous sodium hydroxide and then with water, followed by drying over anhydrous sodium sulfate. The dried solution was distilled under reduced pressure to remove the solvent, and there was afforded imidazol-1-yl-isothioacetic acid 4'-chloro-2'-trifluoromethylanilide S-benzylether (Compound No. 186) as a lightly colored oil in a yield of 38.5 g (94%). This oil was purified in silica gel column chromatography to give a pure product as a colorless oil which showed a refractive index $n_D^{23} = 1.5792$.

EXAMPLE 9

Production of Compound No. 120 of Table 1 and of the formula

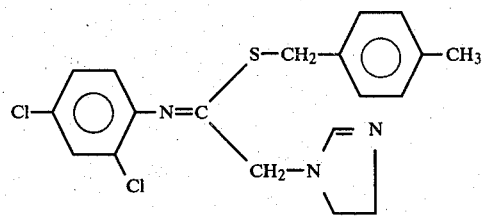

Imidazol-1-yl-thioacetic acid 2',4'-dichloroanilide (28.6 g) of the formula

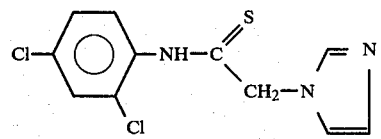

was admixed with a solution in ethanol of sodium ethoxide which was prepared by reacting 2.3 g of metallic sodium with 100 ml of ethanol. To the resultant mixture was then added a solution of p-methylbenzyl chloride (14.1 g) in ethanol (30 ml), and the whole admixture was refluxed for 30 minutes. Subsequent to cooling, the salt deposited was removed from the reaction solution by filtration under sucking, and the filtrate was concentrated under reduced pressure to give imidazol-1-yl-isothioacetic acid 2',4'-dichloroanilide S-p-methylbenzylether (Compound No. 120) as lightly yellow colored crystals in a yield of 38.2 g. Recrystallization from a mixed solvent of cyclohexane/acetone gave the pure product as colorless crystals which showed a melting point of 77°–78.5° C.

EXAMPLE 10

Production of Compound No. 103 of Table 1 and of the formula

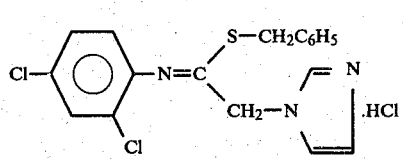

Imidazol-1-yl-isothioacetic acid 2',4'-dichloroanillide S-benzylether (3.8 g) of the formula

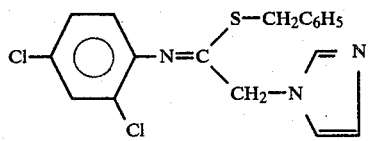

was dissolved in 50 ml of acetone, followed by addition of 2 ml of 5 N hydrochloric acid. The whole admixture obtained was allowed to stand at ambient temperature for one hour. The colorless crystals thus deposited were isolated from the reaction solution by filtration and washed with acetone to afford imidazol-1-yl-isothioacetic acid 2',4'-dichloroanilide S-p-chlorobenzylether hydrochloride (Compound No. 103) as colorless crystals in a yield of 3.5 g, which showed a melting point of 114°–115.5° C.

EXAMPLE 11

Production of Compound No. 116 of Table 1.

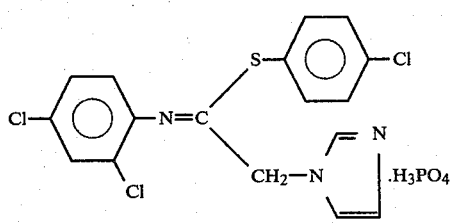

Imidazol-1-yl-isothioacetic acid 2',4'-dichloroanilide S-p-chlorobenzylether (4.1 g) of the formula

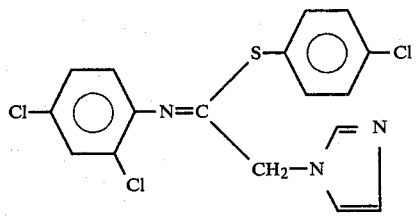

was dissolved in 50 ml of dioxane, followed by addition of 1.5 g of 85% phosphoric acid. The whole admixture obtained was allowed to stand at ambient temperature for one hour. The colorless crystals thus deposited were isolated from the reaction solution by filtration and washed with dioxane to afford imidazol-1-yl-isothioacetic acid 2',4'-dichloroanilide S-p-chlorobenzylether phosphate (Compound No. 116) as colorless crystals in a yield of 4.5 g, which showed a melting point of 158°–159.5° C.

EXAMPLE 12

Production of Compound No. 160 of Table 1.
Imidazol-1-yl-isothioacetic acid 2',4'-dimethylanilide S-ethylether (2.7 g) of the formula

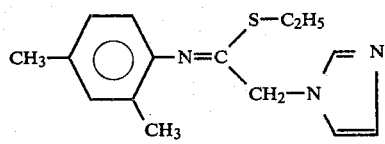

was admixed, with stirring, with a solution of sulfamic acid (1.0 g) in water (100 ml). The whole admixture obtained was stirred at ambient temperature for 10 minutes, and the colorless crystals deposited were isolated from the reaction solution by filtration, washed with water and then dried. There was afforded imidazol-1-yl-isothioacetic acid 2',4'-dimethylanilide S-ethylether sulfamate (Compound No. 160) as colorless crystals in a yield of 3.3 g, which showed a melting point of 140°–141° C.

EXAMPLE 13

Production of Compound No. 86 of Table 1.
Imidazol-1-yl-isoacetic acid 2',4'-dichloroanilide O-n-propylether (3.1 g) of the formula

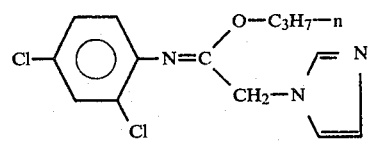

was dissolved in 100 ml of dioxane, and the resultant solution was admixed with 2.0 g of p-toluenesulfonic acid monohydrate with stirring. The whole admixture obtained was stirred at ambient temperature for 30 minutes, and the colorless crystals deposited were isolated from the reaction solution by filtration and washed with dioxane to afford imidazol-1-yl-isoacetic acid 2',4'-dichloroanilide O-n-propylether p-toluenesulfonate (Compound No. 86) as colorless crystals in a yield of 4.4 g, which showed a melting point of 175°–176.5° C.

EXAMPLE 14

Production of Compound No. 105 of Table 1.
Imidazol-1-yl-isothioacetic acid 2',4'-dichloroanilide S-benzylether (3.8 g) of the formula

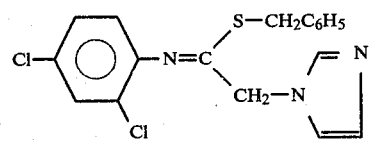

was dissolved in 50 ml of ether, followed by addition of 5.0 g of formic acid. The whole admixture obtained was allowed to stand in a refrigerator for one day. The colorless crystals thus deposited were isolated from the reaction solution by filtration and washed with a small volume of ether to afford imidazol-1-yl-isothioacetic acid 2',4'-dichloroanilide S-benzylether formate (Compound No. 105) as colorless crystals in a yield of 2.9 g, which showed a melting point of 44°–47° C.

EXAMPLE 15

Production of Compound No. 187 of Table 1.
Imidazol-1-yl-isothioacetic acid 4'-chloro-2'-trifluoromethylanilide S-benzylether (4.1 g) of the formula

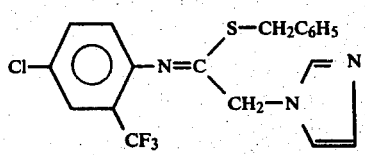

was dissolved in 10 ml of methanol, and the resultant solution was admixed, with stirring, with a solution of oxalic acid (1 g) in water (100 ml). The whole admixture was stirred at ambient temperature for one hour, and the colorless crystals thus deposited were isolated from the reaction solution by filtration, washed with water and dried to give imidazol-1-yl-isothioacetic acid 4'-chloro-2'-trifluoromethylanilide S-benzylether oxalate (Compound No. 187) as colorless crystals in a yield of 4.7 g, which showed a melting point of 146°–147.5° C.

EXAMPLE 16

Production of Compound No. 92 of Table 1 of the formula

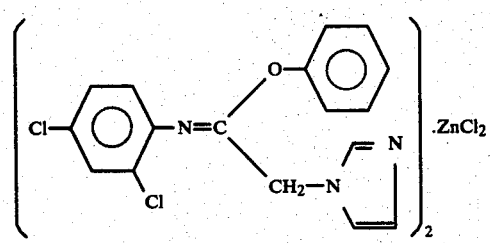

Imidazol-1-yl-isoacetic acid 2',4'-dichloroanilide O-phenylether (3.5 g) of the formula

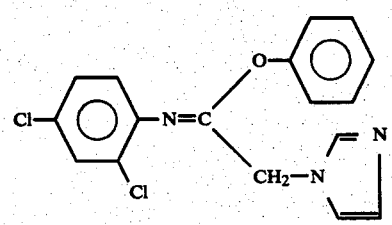

was dissolved in 10 ml of methanol, and the resultant solution was admixed, with stirring, with a solution of zinc chloride (0.7 g) in water (100 ml). The whole admixture was stirred at ambient temperature for 30 minutes, and the colorless crystals deposited were isolated from the reaction solution by filtration and washed with water. There was afforded bis(imidazol-1-yl-isoacetic acid 2',4'-dichloroanilide O-phenylether) zinc chloride (Compound No. 92) as colorless crystals in a yield of 3.6 g, which showed a melting point of 88°–89° C.

EXAMPLE 17

Production of Compound No. 110 of Table 1.

Imidazol-1-yl-isothioacetic acid 2',4'-dichloroanilide S-benzylether (3.8 g) of the formula

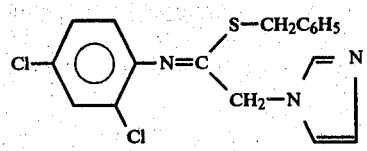

was dissolved in 10 ml of methanol, and the resultant solution was admixed, with stirring, with a solution of manganese dichloride tetrahydrate (1.2 g) in water (100 ml). The whole admixture was allowed to stand at ambient temperature for 3 hours, and the colorless crystals thus deposited were isolated from the reaction solution by filtration and washed with water. There was thus afforded bis(imidazol-1-yl-isothioacetic acid 2',4'-dichloroanilide S-benzylether) manganese dichloride (Compound No. 110) as colorless crystals in a yield of 4.0 g, which showed a melting point of 39°–42° C.

EXAMPLE 18

Production of Compound No. 119 of Table 1.

Imidazol-1-yl-isothioacetic acid 2',4'-dichloroanilide S-p-chlorobenzylether (4.1 g) of the formula

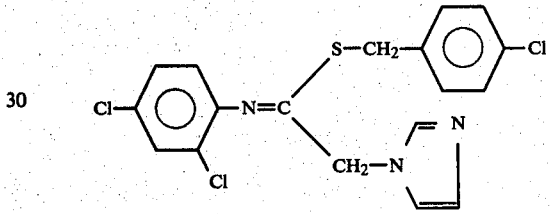

was dissolved in 10 ml of methanol, and the resultant solution was admixed with 0.7 g of anhydrous ferric chloride. The resultant admixture was stirred at ambient temperature for 10 minutes and admixed with 100 ml of water, and the crystals thus deposited were isolated from the reaction solution by filtration. The resultant crystals were washed with water and dried to give tris(imidazol-1-yl-isothioacetic acid 2',4'-dichloroanilide S-p-chlorobenzylether) ferric chloride (Compound No. 119) as colorless crystals in a yield of 4.0 g, which showed a melting point of 116°–117.5° C.

EXAMPLE 19

Production of Compound No. 122 of Table 1.
Imidazol-1-yl-isothioacetic acid 2',4'-dichloroanilide S-p-methylbenzylether (3.9 g) of the formula

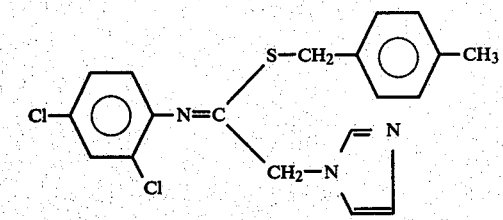

was dissolved in 10 ml of ethyl acetate, and the resultant solution was admixed with 0.8 g of anhydrous cupric chloride. The resultant admixture was stirred at ambient temperature for 10 minutes and then admixed with 100 ml of n-hexane. The crystals deposited were isolated from the reaction solution by filtration and washed with n-hexane to afford bis(imidazol-1-yl-isothioacetic acid 2',4'-dichloroanilide S-p-methylbenzylether) cupric chloride (Compound No. 122) as bluish white colored crystals in a yield of 4.1 g, which showed a melting point of 81°–83° C.

EXAMPLE 20

Production of Compound No. 147 of Table 1.

Imidazol-1-yl-isothioacetic acid 3',5'-dichloroanilide S-benzylether (3.8 g) of the formula

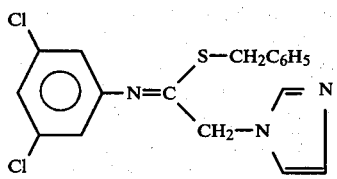

was dissolved in 10 ml of methanol, and the resultant solution was admixed, with stirring, with a solution of ferrous chloride tetrahydrate (2.2 g) in water (100 ml). The whole admixture obtained was allowed to stand for 3 hours, and the crystals deposited were isolated from the reaction solution by filtration, washed with water and dried. There was thus afforded bis(imidazol-1-yl-isothioacetic acid 3',5'-dichloroanilide S-benzylether) ferrous chloride (Compound No. 147) as ocher colored crystals in a yield of 3.7 g, which showed a melting point of 57°–59° C.

Similarly to the procedures of the Examples 1 to 20, further examples of the new compound of the formula [I] were produced. Representative compounds are listed in Table 1 below. In Table 1, the column of "Salts" indicates the nature of the inorganic acid, organic acid or metal salt forming the salts (or complex) of the compound [I] of the invention, as well as the molar proportion of the compound [I] in the free form which are required to constitute one mole of the salt or complex of the compound of the invention. Compound Numbers shown in Table 1 are referred to in the following Examples 21 to 33.

TABLE 1

TABLE 1-continued $$R_1-N=C\begin{matrix}X-R_2\\Y-N\end{matrix}\begin{matrix}\\=N\end{matrix} \text{ and salts thereof}$$

| Compound No. | R₁ | R₂ | X | Y | Salts Salt-forming component | moles | Refractive index or m.p. (°C) |
|---|---|---|---|---|---|---|---|
| 15 | " | —C₂H₅ | S | " | | | $n_D^{23}$ 1.5840 |
| 16 | " | —CH₂—C₆H₅ | " | " | | | $n_D^{23}$ 1.6162 |
| 17 | " | " | " | " | NO₂—C₆H₄—CO₂H | 1 | m.p. 74~76 |
| 18 | " | —CH₂CH=CH₂ | " | —CH—n-C₄H₉ | | | $n_D^{23}$ 1.5712 |
| 19 | " | " | " | " | (CO₂H)₂ | 1 | m.p. 111~112.5 |
| 20 | " | —C₄H₉—i | " | —CH—C₆H₅ | | | $n_D^{23}$ 1.5958 |
| 21 | " | " | " | " | CuCl₂ | 2 | m.p. 63~66 |
| 22 | 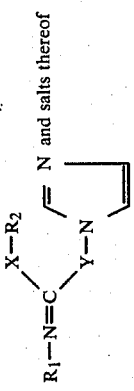 | —C₁₀H₂₁—n | " | —CH₂— | | | $n_D^{23}$ 1.5934 |
| 23 | " | —CH₂—C₆H₅ | O | —CH—CH=CH₂ | | | $n_D^{23}$ 1.5899 |
| 24 | " | —CH₂SCH₃ | S | —CH—CH₂—C₆H₃Cl₂ | | | $n_D^{23}$ 1.5941 |

TABLE 1-continued $R_1-N=C\begin{matrix}X-R_2\\Y-N\end{matrix}\begin{matrix}\\ \diagdown\end{matrix}N$ and salts thereof

| Compound No. | $R_1$ | $R_2$ | X | Y | Salts Salt-forming component | moles | Refractive index or m.p. (°C) |
|---|---|---|---|---|---|---|---|
| 25 | 4-Cl-C$_6$H$_4$ | —CH$_2$CH$_2$S-C$_6$H$_5$ | O | —CH$_2$— | | | $n_D^{23}$ 1.5909 |
| 26 | " | —C$_2$H$_5$ | S | " | | | m.p. 49~51 |
| 27 | " | " | " | " | p-TsOH | 1 | m.p. 147.5~149 |
| 28 | " | —CH$_2$-C$_6$H$_5$ | " | " | | | m.p. 103~104 |
| 29 | " | " | " | " | NH$_2$SO$_3$H | 1 | m.p. 149~150.5 |
| 30 | " | —CH$_2$CH$_2$CH$_2$Cl | " | —CH—<br>n-C$_3$H$_7$ | | | $n_D^{23}$ 1.5876 |
| 31 | " | —C$_2$H$_5$ | " | —CH$_2$— | | | $n_D^{23}$ 1.5856 |
| 32 | 4-F-C$_6$H$_4$ | —CH$_2$-C$_6$H$_5$ | " | " | | | m.p. 73.5~75.5 |
| 33 | " | -C$_6$H$_4$-CH$_3$ | O | " | | | $n_D^{23}$ 1.5981 |
| 34 | 4-Br-C$_6$H$_4$ | n-C$_5$H$_{11}$ | S | " | p-TsOH | 1 | m.p. 161~163.5 |
| 35 | " | " | " | " | | | $n_D^{23}$ 1.5964 |
| 36 | " | " | " | " | (CO$_2$H)$_2$ | 1 | m.p. 134.5~136 |
| 37 | " | —CH$_2$SCH$_3$ | " | " | | | $n_D^{23}$ 1.5918 |
| 38 | 4-NO$_2$-C$_6$H$_4$ | —C$_2$H$_5$ | O | —CH—<br>CH$_2$-C$_6$H$_5$ | | | $n_D^{23}$ 1.5930 |

TABLE 1-continued $R_1-N=C \begin{matrix} X-R_2 \\ Y-N \end{matrix} = N$ and salts thereof

| Compound No. | R₁ | R₂ | X | Y | Salt-forming component | moles | Refractive index or m.p. (°C.) |
|---|---|---|---|---|---|---|---|
| 39 | 4-NC-C₆H₄- | -CH₂-C₆H₄-Cl (4) | S | -CH₂- | | | $n_D^{23}$ 1.5981 |
| 40 | 4-CH₃-C₆H₄- | -C₂H₅ | " | " | | | m.p. 70~72 |
| 41 | " | -CH₂CO₂C₂H₅ | " | " | HCl | 1 | m.p. 142~144 |
| 42 | " | " | " | " | | | $n_D^{23}$ 1.6020 |
| 43 | " | -CH₂-C₆H₅ | " | " | | | m.p. 98~99.5 |
| 44 | " | -CH₂-(tetrahydrofuran-2-yl) | " | " | (C₂H₅O)₂PSH ‖ S | 1 | m.p. 126~128.5 |
| 45 | " | -CH₂-(cyclopentyl) | O | -CH₂CH₂- | | | $n_D^{23}$ 1.5976 |
| 46 | " | -CH₂C(=O)-CH₃ | S | -CH₂- | | | $n_D^{23}$ 1.5842 |
| 47 | " | -CH₂C(=O)-CH₃ | " | -CH(i-C₃H₇)- | | | $n_D^{23}$ 1.5907 |
| 48 | CH₂=CHCH₂- | -CH₂CH₂O-C₆H₄-(4) | " | -CH₂- | | | $n_D^{23}$ 1.5892 |
| 49 | " | -CH₂CN | " | -CH(CH=CH₂)- | | | $n_D^{23}$ 1.5916 |

TABLE 1-continued $$R_1-N=C\begin{matrix}X-R_2\\Y-N\end{matrix}\diagup=\diagdown N \text{ and salts thereof}$$

| Compound No. | R₁ | R₂ | X | Y | Salt-forming component | Salts moles | Refractive index or m.p. (°C.) |
|---|---|---|---|---|---|---|---|
| 50 | 2-CF₃-C₆H₄- | —C₂H₅ | " | —CH₂— | | | $n_D^{23}$ 1.5508 |
| 51 | " | " | " | " | CuSO₄ | 2 | m.p. 79~80.5 |
| 52 | 3-CF₃-C₆H₄- | —CH₂-C₆H₅ | " | " | | | $n_D^{23}$ 1.5679 |
| 53 | " | —C₆H₅ | O | —CH—<br>—CH₂Cl | | | $n_D^{23}$ 1.5801 |
| 54 | 4-CH₃O-C₆H₄- | —CH₂-C(=O)-CH₃ | S | —CH₂— | | | $n_D^{23}$ 1.6004 |
| 55 | " | —CH₂CH₂OC₂H₅ | O | —CH₂CH₂CH₂— | | | $n_D^{23}$ 1.5977 |
| 56 | " | 4-NO₂-C₆H₄- | " | —CH—(4-Cl-C₆H₄)— | | | $n_D^{23}$ 1.5963 |
| 57 | 3-i-C₃H₇O-C₆H₄- | —CH₃ | O | —CH₂— | | | $n_D^{23}$ 1.5894 |
| 58 | " | —C₂H₅ | S | " | | | $n_D^{23}$ 1.5844 |
| 59 | " | " | " | " | (CO₂H)₂ | 1 | m.p. 135.5~138 |
| 60 | " | —CH₂-C₆H₅ | " | " | | | m.p. 67~69 |

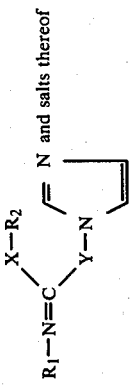

TABLE 1-continued $$R_1-N=C\underset{Y-N}{\overset{X-R_2}{\diagup}}\hspace{-1em}\diagdown\hspace{-0.5em}=\hspace{-0.5em}N \text{ and salts thereof}$$

| Compound No. | $R_1$ | $R_2$ | X | Y | Salt-forming component | moles | Refractive index or m.p. (°C.) |
|---|---|---|---|---|---|---|---|
| 61 | " | —CH₂CH₂NHC₂H₅ | " | " | | | $n_D^{23}$ 1.5849 |
| 62 | " | —CH₂—C₆H₅ | " | —CH(C₆H₁₃-n)— | | | $n_D^{23}$ 1.5906 |
| 63 | i-C₃H₇O—C₆H₄— | —CH₃ | " | —CH(p-CH₃-C₆H₄)— | | | $n_D^{23}$ 1.5942 |
| 64 | CH₂=CHCH₂O—C₆H₄— | —CH₂CH₂SCH₃ | O | —CH₂— | | | $n_D^{23}$ 1.5763 |
| 65 | " | —C₈H₁₇-n | S | " | | | $n_D^{23}$ 1.5911 |
| 66 | CH₃S—C₆H₄— | —CH₂—(p-CH₃-C₆H₄) | " | " | | | $n_D^{23}$ 1.5855 |
| 67 | CH₃SO—C₆H₄— | —C₄H₉-n | " | " | | | $n_D^{23}$ 1.5894 |
| 68 | CH₃SO₂—C₆H₄— | —C₂H₅ | O | " | | | $n_D^{23}$ 1.5814 |
| 69 | " | —CH₂CH=CH₂ | S | " | | | $n_D^{23}$ 1.5842 |
| 70 | " | —CH₂—C₆H₅ | " | " | | | $n_D^{23}$ 1.5865 |
| 71 | " | —CH₂—(p-Cl-C₆H₄) | " | —CH(CH₃)— | | | $n_D^{23}$ 1.5975 |

TABLE 1-continued $$R_1-N=C\begin{smallmatrix}X-R_2\\Y-N\end{smallmatrix}\!\!\!\diagup\!\!\!\diagdown N \text{ and salts thereof}$$

| Compound No. | $R_1$ | $R_2$ | X | Y | Salts: Salt-forming component | Salts: moles | Refractive index or m.p. (°C) |
|---|---|---|---|---|---|---|---|
| 72 | 4-CH$_3$CO-C$_6$H$_4$- | -C$_6$H$_{13}$-n | O | -CH$_2$- | | | $n_D^{23}$ 1.5841 |
| 73 | " | -CH(CH$_3$)-C≡CH | S | " | | | $n_D^{23}$ 1.5863 |
| 74 | " | -CH$_2$-(3,4-Cl$_2$-C$_6$H$_3$) | " | " | | | $n_D^{23}$ 1.5909 |
| 75 | 4-phenyl-C$_6$H$_4$- | -CH$_2$-(4-Cl-C$_6$H$_4$) | " | " | | | $n_D^{23}$ 1.6026 |
| 76 | 4-(4-Cl-C$_6$H$_4$O)-C$_6$H$_4$- | -C$_5$H$_{11}$-n | O | " | | | $n_D^{23}$ 1.6041 |
| 77 | 4-(C$_6$H$_5$S)-C$_6$H$_4$- | -CH$_2$-(4-Cl-C$_6$H$_4$) | S | " | | | $n_D^{23}$ 1.6002 |
| 78 | 4-(4-CH$_3$-C$_6$H$_4$S)-C$_6$H$_4$- | -CH$_2$-(4-CH$_3$-C$_6$H$_4$) | " | -CH(CH$_3$)- | | | $n_D^{23}$ 1.5998 |
| 79 | 4-(4-NO$_2$-C$_6$H$_4$S)-C$_6$H$_4$- | -CH$_2$-(4-CH$_3$-C$_6$H$_4$) | " | -CH$_2$- | | | $n_D^{23}$ 1.6060 |
| 80 | " | -C$_2$H$_5$ | O | " | | | $n_D^{23}$ 1.5973 |

TABLE 1-continued $R_1-N=C\diagdown^{X-R_2}_{Y-N}$ N and salts thereof (pyrrole ring)

| Compound No. | R₁ | R₂ | X | Y | Salts Salt-forming component | moles | Refractive index or m.p. (°C) |
|---|---|---|---|---|---|---|---|
| 81 | 2,4-diCl-C₆H₃ | —CH₃ | O | " | | | $n_D^{23}$ 1.5866 |
| 82 | " | —C₂H₅ | " | " | (CO₂H)₂ | 1 | m.p. 160~162 |
| 83 | " | " | " | " | CuCl₂ | 2 | $n_D^{23}$ 1.5772 |
| 84 | " | —C₃H₇-n | " | " | | | $n_D^{23}$ 1.5686 |
| 85 | " | " | " | " | p-TsOH | 1 | m.p. 175~176.5 |
| 86 | " | —H | " | " | | | $n_D^{23}$ 1.5128 |
| 87 | " | —C₆H₅ | " | " | | | |
| 88 | " | " | " | " | H₃PO₄ | 1 | m.p. 124~126 |
| 89 | " | —CH₂—C₆H₅ | " | " | | | $n_D^{23}$ 1.5664 |
| 90 | " | " | " | " | CHCO₂H∥CHCO₂H | 1 | m.p. 112.5~114 |
| 91 | " | —C₆H₅ | S | " | | | $n_D^{23}$ 1.5931 |
| 92 | " | —CH₃ | " | " | | | m.p. 88~91 |
| 93 | " | —C₂H₅ | " | " | | | $n_D^{23}$ 1.5922 |
| 94 | " | —C₃H₇-n | " | " | | | m.p. 95.5~97 |
| 95 | " | —C₃H₇-i | " | " | | | $n_D^{23}$ 1.5936 |
| 96 | " | " | " | " | | | m.p. 64~65.5 |
| 97 | " | " | " | " | ZnCl₂ | 2 | m.p. 116.5~119 |
| 98 | " | —C₄H₉-n | " | " | | | $n_D^{23}$ 1.6161 |
| 99 | " | —CH₂CH=CH₂ | " | " | HBr | 1 | $n_D^{23}$ 1.6126 |
| 100 | " | " | " | " | | | m.p. 123~125.5 |
| 101 | " | —C₆H₅ | " | " | (CO₂H)₂ | 1 | $n_D^{23}$ 1.5821 |

TABLE 1-continued $R_1-N=C{<}^{X-R_2}_{Y-N}\!\!=\!\!N$ and salts thereof

| Compound No. | R₁ | R₂ | X | Y | Salt-forming component | Salts moles | Refractive index or m.p. (°C.) |
|---|---|---|---|---|---|---|---|
| 102 | " | —CH₂—⟨phenyl⟩ | " | " | | | $n_D^{23}$ 1.6411 |
| 103 | " | " | " | " | HCl | 1 | m.p. 114~115.5 |
| 104 | " | " | " | " | H₃PO₄ | " | m.p. 160~161 |
| 105 | " | " | " | " | HCO₂H | " | m.p. 44~47 |
| 106 | " | " | " | " | (CO₂H)₂ | " | m.p. 169~170 |
| 107 | " | " | " | " | CHCO₂H=CHCO₂H | 1 | m.p. 99~100.5 |
| 108 | " | " | " | " | CuCl₂ | 2 | m.p. 72~74.5 |
| 109 | " | " | " | " | CuSO₄ | " | m.p. 65~66 |
| 110 | " | " | " | " | MnCl₂ | " | m.p. 39~42 |
| 111 | " | " | " | " | ZnCl₂ | " | m.p. 68~70 |
| 112 | " | " | " | " | CoCl₂ | " | m.p. 63~65 |
| 113 | " | " | " | " | NiCl₂ | " | m.p. 76~78 |
| 114 | " | " | " | " | FeCl₂ | " | m.p. 60~62.5 |
| 115 | " | —CH₂—⟨4-Cl-phenyl⟩ | " | " | | | m.p. 94~95 |
| 116 | " | " | " | " | H₃PO₄ | 1 | m.p. 158~159.5 |
| 117 | " | " | " | " | NH₂SO₃H | " | m.p. 63~65 |
| 118 | " | " | " | " | (CO₂H)₂ | " | m.p. 121~122 |
| 119 | " | " | " | " | FeCl₃ | 3 | m.p. 116~117.5 |
| 120 | " | —CH₂—⟨4-CH₃-phenyl⟩ | " | " | | | m.p. 77~78.5 |
| 121 | " | " | " | " | HCl | 1 | m.p. 122~123.5 |
| 122 | " | " | " | " | CuCl₂ | 2 | m.p. 81~83 |
| 123 | " | ⟨phenyl⟩ | " | " | | | $n_D^{23}$ 1.5681 |

TABLE 1-continued $$R_1-N=C\underset{Y-N}{\overset{X-R_2}{\diagup}} \diagdown\hspace{-0.5em}= N \text{ and salts thereof}$$

| Compound No. | $R_1$ | $R_2$ | X | Y | Salts Salt-forming component | moles | Refractive index or m.p. (°C.) |
|---|---|---|---|---|---|---|---|
| 124 | " | —CCH$_3$ ‖ O | " | " | | | $n_D^{23}$ 138~139 |
| 125 | " | —C$_6$H$_5$—C(=O)— | " | " | | | $n_D^{23}$ 1.5735 |
| 126 | " | —CH$_3$ | O | —CH— CH$_3$ | | | $n_D^{23}$ 1.5945 |
| 127 | " | —C$_6$H$_5$ | " | " | | | $n_D^{23}$ 1.6002 |
| 128 | " | —CH$_3$ | S | " | | | $n_D^{23}$ 1.6129 |
| 129 | " | " | " | " | (CO$_2$H)$_2$ | 1 | m.p. 143~145 |
| 130 | " | —C$_2$H$_5$ | " | " | | | $n_D^{23}$ 1.6003 |
| 131 | " | —C$_3$H$_7$—n | " | " | | | $n_D^{23}$ 1.5928 |
| 132 | " | —C$_4$H$_9$—n | " | " | | | $n_D^{23}$ 1.5925 |
| 133 | " | " | " | " | CuCl$_2$ | 2 | m.p. 51~53.5 |
| 134 | " | —CH$_2$—C$_6$H$_5$ | " | " | | | m.p. 74~75 |
| 135 | " | " | " | " | p-TsOH | 1 | m.p. 154~156 |
| 136 | " | —C$_6$H$_5$ | " | " | | | $n_D^{23}$ 1.6210 |
| 137 | " | " | " | " | ZnCl$_2$ | 2 | m.p. 58~61 |
| 138 | " | —CH$_2$—C$_6$H$_5$ | " | —CH— C$_2$H$_5$ | | | $n_D^{23}$ 1.5845 |

TABLE 1-continued $R_1-N=C\begin{smallmatrix}X-R_2\\Y-N\end{smallmatrix}\!\!=\!\!N$ and salts thereof

| Compound No. | R₁ | R₂ | X | Y | Salts: Salt-forming component | Salts: moles | Refractive index or m.p. (°C) |
|---|---|---|---|---|---|---|---|
| 139 | " | 4-Cl-C₆H₄ | O | —CH(C₄H₉-n)— | | | $n_D^{23}$ 1.6040 |
| 140 | " | 4-CH₃-C₆H₄ | " | —CH(C₆H₅)— | | | $n_D^{23}$ 1.5942 |
| 141 | 2,4-Cl₂-C₆H₃ | 4-CN-C₆H₄ | " | —CH₂— | | | $n_D^{23}$ 1.5894 |
| 142 | " | —CH₂SCH₃ | S | " | | | $n_D^{23}$ 1.5886 |
| 143 | " | —CH₂CH₂-(4-CH₃-C₆H₄) | " | —CH₂—CH=CH— | | | $n_D^{23}$ 1.5873 |
| 144 | 3,5-Cl₂-C₆H₃ | 4-Cl-C₆H₄ | O | —CH₂— | | | $n_D^{23}$ 1.5983 |
| 145 | " | —C₂H₅ | S | " | | | $n_D^{23}$ 1.6081 |
| 146 | " | —CH₂-C₆H₅ | " | " | | | $n_D^{23}$ 1.6290 |
| 147 | " | " | " | " | FeCl₂ | 2 | m.p. 57~59 |
| 148 | " | —CH₂CH₂N(pyrrolidine) | " | " | | | $n_D^{23}$ 1.6052 |

TABLE 1-continued $$R_1-N=C{\overset{X-R_2}{\underset{Y-N}{\Big\langle}}}\overset{\displaystyle}{=\!\!=}N \text{ and salts thereof}$$

| Compound No. | $R_1$ | $R_2$ | X | Y | Salt-forming component | moles | Refractive index or m.p. (°C.) |
|---|---|---|---|---|---|---|---|
| 149 | " | $-CH_2-C=CH_2$<br>    $\quad\ \|$<br>    $\quad CH_3$ | " | $-CH-$<br>  $\|$<br>  $CH_2OCH_3$ | | | $n_D^{23}$ 1.6024 |
| 150 | 2,4-dibromophenyl (3-Br, 4-Br) | $-C_4H_9-t$ | " | $-CH_2-$ | | | $n_D^{23}$ 1.5943 |
| 151 | " | $-CH_2OCH_3$ | " | $-CH-$<br>   2,4-dichlorophenyl | | | $n_D^{23}$ 1.5889 |
| 152 | 2-chloro-4-bromophenyl | $-C_3H_7-i$ | " | $-CH_2-$ | | | $n_D^{23}$ 1.5950 |
| 153 | " | $-CH_2C(=O)-C_6H_5$ | " | | | | $n_D^{23}$ 1.5963 |
| 154 | " | $-C_6H_4-CH_3$ (p-tolyl) | O | $-CH-$<br>  $\|$<br>  $CH_3$ | | | $n_D^{23}$ 1.5951 |
| 155 | 2-fluoro-4-chlorophenyl | 1-naphthyl | " | $-CH-$<br>  $\|$<br>  $C_4H_9-i$ | | | $n_D^{23}$ 1.5843 |
| 156 | " | $-CH_2C{\equiv}CH$ | S | $-CH_2-$ | | | $n_D^{23}$ 1.5887 |

TABLE 1-continued $$R_1-N=C\begin{matrix}X-R_2\\Y-N\end{matrix}\begin{matrix}\\=\\\end{matrix}N \text{ and salts thereof}$$

| Compound No. | $R_1$ | $R_2$ | X | Y | Salts Salt-forming component | moles | Refractive index or m.p. (°C.) |
|---|---|---|---|---|---|---|---|
| 157 | " | —C$_4$H$_9$—n | " | —CH—<br>\|<br>CH$_2$CN | | | $n_D^{23}$ 1.5892 |
| 158 | 2,4-(CH$_3$)$_2$C$_6$H$_3$— | —CH$_2$CH$_2$O-(2,4-Cl$_2$C$_6$H$_3$) | O | —CH$_2$— | | | $n_D^{23}$ 1.5946 |
| 159 | " | —C$_2$H$_5$ | S | " | | | $n_D^{23}$ 1.5856 |
| 160 | " | " | " | " | NH$_2$SO$_3$H | 1 | m.p. 140~141 |
| 161 | " | —CH$_2$—C$_6$H$_5$ | " | " | | | m.p. 70.5~72 |
| 162 | " | " | " | " | 4-NO$_2$-C$_6$H$_4$-CO$_2$H | 1 | m.p. 100~102 |
| 163 | " | —C$_2$H$_5$ | " | —CH—<br>\|<br>CH$_3$ | | | $n_D^{23}$ 1.6027 |
| 164 | " | —CH$_2$—C$_6$H$_5$ | O | —CH—<br>\|<br>C$_6$H$_5$ | | | $n_D^{23}$ 1.5983 |
| 165 | 2,6-(CH$_3$)$_2$C$_6$H$_3$— | furfuryl-CH$_2$— | " | —CH$_2$— | | | $n_D^{23}$ 1.5899 |
| 166 | " | —C$_2$H$_5$ | S | " | | | $n_D^{23}$ 1.5390 |

TABLE 1-continued $$R_1-N=C\begin{matrix}X-R_2\\Y-N\end{matrix}\diagup\hspace{-0.5em}=\hspace{-0.5em}\diagdown N \text{ and salts thereof}$$

| Compound No. | R₁ | R₂ | X | Y | Salts Salt-forming component | moles | Refractive index or m.p. (°C.) |
|---|---|---|---|---|---|---|---|
| 167 | " | —CH₂—⌬ | " | " | | | m.p. 83.5~85.5 |
| 168 | " | —CH₂CO₂C₂H₅ | " | " | p-TsOH | 1 | m.p. 179~181 |
| 169 | " | " | " | —CH—CH₃ | | | $n_D^{23}$ 1.5468 |
| 170 | " | —C(=O)CH₃ | " | —CH—⌬ | (CO₂H)₂ | 1 | m.p. 61~64 |
| 171 | " | ⌬—CH₃ | " | " | | | $n_D^{23}$ 1.5878 |
| 172 | 2-OCH₃-3-CH₃-5-CH₃O-phenyl | —C₂H₅ | O | —CH₂— | | | $n_D^{23}$ 1.5907 |
| 173 | " | " | S | " | (CO₂H)₂ | 1 | $n_D^{23}$ 1.5889 |
| 174 | " | " | " | " | p-TsOH | " | m.p. 136~138 |
| 175 | " | " | " | " | | | m.p. 130.5~132 |
| 176 | 3-Cl-4-CH₃-phenyl-CH₂ | 2,4-Cl₂-phenyl-CH₂ | O | " | | | $n_D^{23}$ 1.6029 |
| 177 | " | —C₁₀H₂₁-n | S | " | | | $n_D^{23}$ 1.5994 |
| 178 | " | ⌬—H | " | —CH—CH₂—CH₃ | | | $n_D^{23}$ 1.5849 |
| 179 | " | " | " | —CH₂—CH—CH₃ | | | $n_D^{23}$ 1.5820 |

TABLE 1-continued $R_1-N=C\begin{matrix}X-R_2\\Y-N\end{matrix}=N$ and salts thereof

| Compound No. | $R_1$ | $R_2$ | X | Y | Salts Salt-forming component | moles | Refractive index or m.p. (°C.) |
|---|---|---|---|---|---|---|---|
| 180 | 2-CH₃-4-Cl-5-CF₃-phenyl | —CH₃— | O | —CH₂— | | | $n_D^{23}$ 1.5836 |
| 181 | " | —C₄H₉—n | S | " | | | $n_D^{23}$ 1.5900 |
| 182 | " | —C₂H₅ | " | " | | | $n_D^{23}$ 1.5631 |
| 183 | " | " | " | " | H₃PO₄ | 1 | m.p. 181 |
| 184 | " | —C₃H₇—n | " | " | | | $n_D^{23}$ 1.6139 |
| 185 | " | phenyl | " | " | | | $n_D^{23}$ 1.5820 |
| 186 | " | —CH₂-phenyl | " | " | | | $n_D^{23}$ 1.5792 |
| 187 | " | " | " | " | (CO₂H)₂ | 1 | m.p. 146~147.5 |
| 188 | " | " | " | " | p-TsOH | " | m.p. 118~121 |
| 189 | " | —CH₂-(4-Cl-phenyl) | " | " | | | $n_D^{23}$ 1.5881 |
| 190 | " | —CH₂-(4-CH₃-phenyl) | " | " | | | $n_D^{23}$ 1.5948 |
| 191 | " | 3-CH₃-phenyl | " | " | | | $n_D^{23}$ 1.5685 |
| 192 | " | " | O | —CH—CH₃ | | | $n_D^{23}$ 1.5937 |
| 193 | " | —CH₂-phenyl | S | " | | | $n_D^{23}$ 1.5949 |

TABLE 1-continued $$R_1-N=C\underset{Y-N}{\overset{X-R_2}{<}}=N \text{ and salts thereof}$$

| Compound No. | R₁ | R₂ | X | Y | Salt-forming component | Salts moles | Refractive index or m.p. (°C) |
|---|---|---|---|---|---|---|---|
| 194 | " | —CH₃ | " | —CH(C₄H₉-n)— | | | $n_D^{23}$ 1.5958 |
| 195 | " | —C₂H₅ | " | —CH(C₆H₅)— | | | $n_D^{23}$ 1.5946 |
| 196 | " | —C₅H₁₁-n | " | —CH₂CH₂— | | | $n_D^{23}$ 1.5955 |
| 197 | 4-Cl, 2-CH₃, 5-OCH₃-C₆H₂ | 2,4-Cl₂-C₆H₃ | O | —CH₂— | | | $n_D^{23}$ 1.5964 |
| 198 | " | —CH₂CH₂S(C₆H₅) | S | " | | | $n_D^{23}$ 1.5843 |
| 199 | 2,4,5-Cl₃-C₆H₂ | —C₄H₉-i | O | " | | | $n_D^{23}$ 1.5826 |
| 200 | " | —C₂H₅ | S | " | H₂SO₄ | | m.p. 81~83 |
| 201 | " | " | " | " | CH₃COCO₂H | 1 | m.p. 142~144 |
| 202 | " | " | " | " | " | " | m.p. 66~68.5 |
| 203 | " | —CH₂C₆H₅ | " | " | | | m.p. 98~99 |
| 204 | " | " | " | " | CuSO₄ | 2 | m.p. 74~6 |

TABLE 1-continued $$R_1-N=C\begin{array}{c}X-R_2\\Y-N\end{array}\!\!\diagdown\!\!=\!\!\diagup N \text{ and salts thereof}$$

| Compound No. | R₁ | R₂ | X | Y | Salts Salt-forming component | moles | Refractive index or m.p. (°C.) |
|---|---|---|---|---|---|---|---|
| 205 | " | −C(=O)−C₆H₅ | " | " | | | $n_D^{23}$ 1.5840 |
| 206 | 2,4,6-trichloro-3,5-dimethylphenyl | −CH₂CH₂OC₂H₅ | " | −CH(C₃H₇-n)− | | | $n_D^{23}$ 1.5852 |
| 207 | " | −CH₂CH=CHCH₃ | O | −CH(C₆H₅)− | | | $n_D^{23}$ 1.5916 |
| 208 | 2,4,6-trichloro-3,5-dimethylphenyl | −C₃H₇-i | S | −CH₂− | | | $n_D^{23}$ 1.5873 |
| 209 | " | −CH₂CO₂C₂H₅ | O | −CH(CH₂C₆H₅)− | | | $n_D^{23}$ 1.5792 |
| 210 | 8-methyl-1-naphthyl | −CH₃ | " | −CH₂− | | | $n_D^{23}$ 1.5944 |
| 211 | " | −C₂H₅ | S | " | | | $n_D^{23}$ 1.6387 |
| 212 | " | −CH₂C₆H₅ | " | " | | | $n_D^{23}$ 1.6489 |

TABLE 1-continued $R_1-N=C\begin{smallmatrix}X-R_2\\Y-N\end{smallmatrix}=N$ and salts thereof

| Compound No. | $R_1$ | $R_2$ | X | Y | Salts Salt-forming component | moles | Refractive index or m.p. (°C.) |
|---|---|---|---|---|---|---|---|
| 213 | " | " | " | " | CHCO$_2$H ‖ CHCO$_2$H | 1 | m.p. 107~110 |
| 214 | " | " | " | " | CuCl$_2$ | 2 | m.p. 68~70 |
| 215 | " | —CH$_2$CH$_2$CH$_2$Cl | " | —CH— C$_2$H$_5$ | | | $n_D^{23}$ 1.5888 |
| 216 | —CH$_2$— | —C$_2$H$_5$ | " | —CH$_2$— | | | $n_D^{23}$ 1.5767 |
| 217 | " | —CH$_2$— | " | " | (CO$_2$H)$_2$ | 1 | m.p. 84~86.5 $n_D^{23}$ 1.6111 |
| 218 | " | —C$_6$H$_{13}$—n | O | " | | | m.p. 42~45 $n_D^{23}$ 1.5821 |
| 219 | " | —CH$_2$CH$_2$N(C$_2$H$_5$)$_2$ | S | —CH— C$_3$H$_7$—i | ZnCl$_2$ | 2 | $n_D^{23}$ 1.5804 |
| 220 | 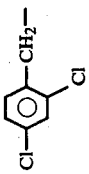 | —CH— CH$_3$ | " | —CH— C$_5$H$_{11}$—n | | | $n_D^{23}$ 1.6021 |
| 221 | | | | | | | |
| 222 | | | | | | | |
| 223 | —CH$_2$CH$_2$— | —CH$_3$ | O | —CH$_2$— | | | $n_D^{23}$ 1.6111 |

TABLE 1-continued $R_1-N=C\begin{smallmatrix}X-R_2\\Y-N\end{smallmatrix}\!\!\diagdown\!\!N$ and salts thereof

| Compound No. | R₁ | R₂ | X | Y | Salts Salt-forming component | moles | Refractive index or m.p. (°C.) |
|---|---|---|---|---|---|---|---|
| 224 | —C₂H₅ | 2,4-di-Cl-C₆H₃— | | —CH(p-NO₂-C₆H₄)— | | | $n_D^{23}$ 1.5794 |
| 225 | —C₄H₉—i | —CH₂CH₂—C₆H₅ | S | —CH₂— | | | $n_D^{23}$ 1.5796 |
| 226 | —C₈H₁₇—n | —CH₂CH=CH—CH=CH—CH₃ | O | —CH(n-C₄H₉)— | | | $n_D^{23}$ 1.5751 |
| 227 | —CH₂CH=CH₂ | furfuryl (—CH₂-furan) | S | —CH(p-Cl-C₆H₄-CH₂)— | | | $n_D^{23}$ 1.5780 |
| 228 | —CH₂CH₂OC₂H₅ | —CH₂CH₂—C₆H₁₁ | " | " | | | $n_D^{23}$ 1.5996 |
| 229 | —CH₂CH₂S—C₆H₅ | —CH₂—C₆H₅—Cl | " | —CH(m-CF₃-C₆H₄)— | | | $n_D^{23}$ 1.5804 |
| 230 | 2-F-C₆H₄-CH₃— | —CH₂—C₆H₄—Cl | " | —CH₂— | | | $n_D^{23}$ 1.6218 |
| 231 | 2,4-di-Cl-C₆H₃-CH₃— | —CH₂—C₆H₄—F | " | " | | | m.p. 77~79 |

TABLE 1-continued
$$R_1-N=C\begin{smallmatrix}X-R_2\\ \\Y-N\end{smallmatrix}\!\!\!\diagup\!\!\!=\!\!\!N \text{ and salts thereof}$$
| Compound No. | R₁ | R₂ | X | Y | Salts Salt-forming component | moles | Refractive index or m.p. (°C.) |
|---|---|---|---|---|---|---|---|
| 232 | " | 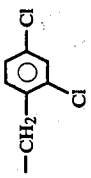 | " | " | | | m.p. 113~115.5 |
| 233 | " | 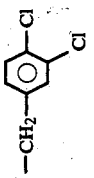 | " | " | | | m.p. 69.5~71 |
| 234 | " | 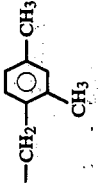 | " | " | | | m.p. 62~65 |
| 235 | " | 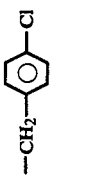 | " | —CH—<br>\|<br>CH₃ | | | m.p. 70.5~73 |
| 236 | " | 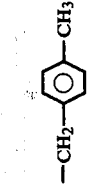 | " | " | | | m.p. 74.5~76 |
| 237 | " | 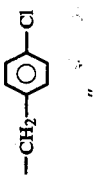 | " | " | | | m.p. 69.5~71.5 |
| 238 | " |  | " | —CH—<br>\|<br>CH₂CH₃ | | | $n_D^{23}$ 1.6242 |
| 239 | 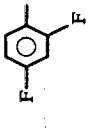 | " | " | —CH₂— | | | m.p. 66.5~68 |

TABLE 1-continued
$R_1-N=C\begin{smallmatrix}X-R_2\\Y-N\end{smallmatrix}\!\!\!=\!\!\!N$ and salts thereof
| Compound No. | $R_1$ | $R_2$ | X | Y | Salts Salt-forming component | moles | Refractive index or m.p. (°C.) |
|---|---|---|---|---|---|---|---|
| 240 | 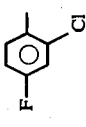 | —CH$_2$—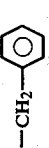 | " | " | | | $n_D^{23}$ 1.6212 |
| 241 | " | —CH$_2$—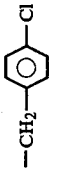—Cl | " | " | | | $n_D^{23}$ 1.6235 |
| 242 | 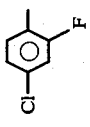 | —CH$_2$— | " | " | | | m.p. 67.5~69.5 |
| 243 | " | —CH$_2$——Cl | " | " | | | m.p. 99~101 |
| 244 | 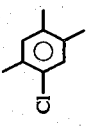 | " | " | " | | | m.p. 102~103 |
Note:
p-TsOH denotes p-toluenesulfonic acid in the above table.

The following Examples 21 to 26 illustrate the procedures for preparing the fungicidal compositions of this invention but are not limitative of this invention. In Examples 21 to 26, "parts" are given by weight.

EXAMPLE 21

Wettable Powder

20 Parts of Compound No. 115, 5 parts of polyoxyethylene alkylarylethers, 3 parts of calcium ligninsulfonate and 72 parts of diatomaceous earth were mixed together and ground uniformly to give a wettable powder containing 20% by weight of the active ingredient compound.

EXAMPLE 22

Emulsifiable Concentrate

30 Parts of Compound No. 102, 50 parts of xylene and 20 parts of polyoxyethylene alkylarylethers were mixed together to make a uniform dissolution, affording an emulsifiable concentrate containing 30% by weight of the active ingredient compound.

EXAMPLE 23

Oily Formulation

50 Parts of Compound No. 85 and 50 parts of ethyl cellosolve were mixed together to make a uniform dissolution, affording an oily formulation containing 50% by weight of the active ingredient compound.

EXAMPLE 24

Sol (Flowable Powder)

40 Parts of finely divided Compound No. 106 having average particle size of not more than 10 microns, 2 parts of lauryl sulfate, 2 parts of sodium alkylnaphthalenesulfonate, 1 part of hydroxypropylcellulose and 55 parts of water were mixed together uniformly to give a sol containing 40% by weight of the active ingredient compound.

EXAMPLE 25

Dusting Powder 0.5 Parts of Compound No. 212, 0.5 parts of finely divided silica, 0.5 parts of calcium stearate, 50 parts of clay and 48.5 parts of talc were mixed together and ground uniformly to give a dusting powder containing 1% of the active ingredient compound.

EXAMPLE 26

Granules 3 Parts of Compound No. 186, 1 part of calcium ligninsulfonate, 30 parts of bentonite and 66 parts of clay were mixed together and ground uniformly. The powdery mixture obtained was granulated with addition of water, followed by drying and screening. Granules containing 3% of the active ingredient compound were obtained.

EXAMPLE 27

This Example illustrate tests of controlling leaf rust in wheat for preventative treatment.

Wheat plants (variety: Norin No. 61) were grown in soil in 9 cm-diameter porous pots in a greenhouse. At the first true-leaf stage, the wheat seedlings were sprayed with the composition under test which was prepared by diluting the wettable powder of the Example 21 with water to a particular concentration of the active compound indicated in Table 2 below. The rate of application of the composition sprayed was 20 ml per three pots. One day after the treatment, the treated foliage was sprayed for inoculation with a suspension of uredospores of wheat leaf rust fungi (*Puccinis recondita*) at such inoculum size that the number of the uredospores on the slide glass observed within the vision field of a microscope (x 150) amounted to approximately 50. The spore suspension used was prepared by suspending the uredospores which were previously produced on another wheat leave, into a volume of sterilized water containing 50 ppm. of a dispersion agent "Tween 20" (a trade name of polyoxyethylene sorbitan monolaurate, a product of Kao Atlas Co., Japan). The inoculated wheat plants were incubated overnight in a high-humidity room at 20° C. and then transferred into a greenhouse at 20° C. in which the environment was appropriate to allow the infection to take place. 10 Days after the inoculation, the infected wheat plants were removed out of the greenhouse and estimated for the degree of disease development. To this end, the number of the uredosorus per leaf was assessed and the degree of control (%) was evaluated according to the under-mentioned equation. The degree of phyto-toxicity of the test compound to wheat plant was assessed according to the under-mentioned grading. The tests were conducted with three replicates for a particular value of the concentration of the test compound, and the average of the evaluated degree of control (%) was calculated. The test results (expressed as averaged Control (%) are set out in Table 2 below.

$$\text{Control (\%)} = \left( 1 - \frac{\text{Number of uredosorus in treated plot}}{\text{Number of uredosorus in non-treated plot}} \right) \times 100$$

Grades for estimation of phyto-toxicity
5—Very much severe
4—Severe
3—Strong
2—Slight
1—Very slight
0—None

EXAMPLE 28

This Example illustrates tests of controlling powdery mildew in cucumber.

Cucumber plants (variety: Sagami-Hanjiro) were grown in soil in 9 cm-diameter porous pots in a greenhouse. At the first true-leaf stage, the cucumber seedlings were sprayed with 10 ml per pot of the composition under test which was prepared by diluting the wettable powder of the Example 21 with water to a particular concentration of the active compound indicated in Table 2 below. The treated cucumber plants were allowed to stand overnight and then sprayed for inoculation with a suspension of spores of cucumber powdery mildew fungi (*Sphaerotheca fuliginea*). 10 Days after the inoculation, the rate (%) of the area of the symptom on the infected leave was assessed, and the degree of control (%) was evaluated according to the under-mentioned equation. The degree of phyto-toxicity of the test compound to cucumber plant was estimated by the same grading as in Example 27. The tests were conducted with three replicates. The test results (expressed as averaged % Control) are given in Table 2.

$$\text{Control (\%)} = \left(1 - \frac{\text{Rate of area of symptom in treated plot}}{\text{Rate of area of symptom in non-treated plot}}\right) \times 100$$

TABLE 2

| Compound No. | Control (%) Concentration of active ingredient compound sprayed (ppm) | | Phytotoxicity | |
|---|---|---|---|---|
| | Leaf rust on wheat 50 | Powdery mildew on cucumber 50 | Wheat | Cucumber |
| 1 | 95 | 97 | 0 | 0 |
| 2 | 92 | 95 | " | " |
| 3 | 97 | 98 | " | " |
| 4 | 100 | 100 | " | " |
| 5 | 99 | 100 | " | " |
| 6 | 94 | 94 | " | " |
| 7 | 100 | 100 | " | " |
| 8 | 100 | 100 | " | " |
| 9 | 93 | 100 | " | " |
| 10 | 95 | 96 | " | " |
| 11 | 100 | 100 | " | " |
| 12 | 90 | 95 | " | " |
| 13 | 89 | 90 | " | " |
| 14 | 98 | 99 | " | " |
| 15 | 100 | 100 | " | " |
| 16 | 100 | 100 | " | " |
| 17 | 100 | 100 | " | " |
| 18 | 99 | 100 | " | " |
| 19 | 98 | 100 | " | " |
| 20 | 95 | 97 | " | " |
| 21 | 95 | 90 | " | " |
| 22 | 92 | 90 | " | " |
| 23 | 93 | 95 | " | " |
| 24 | 90 | 92 | " | " |
| 25 | 98 | 98 | " | " |
| 26 | 100 | 100 | " | " |
| 27 | 100 | 100 | " | " |
| 28 | 100 | 100 | " | " |
| 29 | 100 | 100 | " | " |
| 30 | 95 | 96 | " | " |
| 31 | 98 | 100 | " | " |
| 32 | 100 | 100 | " | " |
| 33 | 100 | 100 | " | " |
| 34 | 99 | 99 | " | " |
| 35 | 100 | 100 | " | " |
| 36 | 100 | 98 | " | " |
| 37 | 97 | 96 | " | " |
| 38 | 95 | 94 | " | " |
| 39 | 90 | 91 | " | " |
| 40 | 99 | 100 | " | " |
| 41 | 98 | 100 | " | " |
| 42 | 87 | 85 | " | " |
| 43 | 100 | 90 | " | " |
| 44 | 97 | 96 | " | " |
| 45 | 92 | 93 | " | " |
| 46 | 94 | 92 | " | " |
| 47 | 92 | 93 | " | " |
| 48 | 91 | 92 | " | " |
| 49 | 94 | 95 | " | " |
| 50 | 100 | 100 | " | " |
| 51 | 100 | 99 | " | " |
| 52 | 100 | 100 | " | " |
| 53 | 95 | 96 | " | " |
| 54 | 92 | 94 | " | " |
| 55 | 93 | 91 | " | " |
| 56 | 85 | 90 | " | " |
| 57 | 98 | 96 | " | " |
| 58 | 100 | 100 | " | " |
| 59 | 100 | 100 | " | " |
| 60 | 100 | 100 | " | " |
| 61 | 98 | 96 | " | " |
| 62 | 100 | 99 | " | " |
| 63 | 93 | 94 | " | " |
| 64 | 91 | 93 | " | " |
| 65 | 93 | 90 | " | " |
| 66 | 98 | 99 | " | " |

TABLE 2-continued

| Compound No. | Control (%) Concentration of active ingredient compound sprayed (ppm) | | Phytotoxicity | |
|---|---|---|---|---|
| | Leaf rust on wheat 50 | Powdery mildew on cucumber 50 | Wheat | Cucumber |
| 67 | 100 | 100 | " | " |
| 68 | 97 | 100 | " | " |
| 69 | 100 | 100 | " | " |
| 70 | 100 | 100 | " | " |
| 71 | 100 | 100 | " | " |
| 72 | 92 | 93 | " | " |
| 73 | 100 | 100 | " | " |
| 74 | 99 | 100 | " | " |
| 75 | 98 | 99 | " | " |
| 76 | 88 | 83 | " | " |
| 77 | 90 | 87 | " | " |
| 78 | 96 | 98 | " | " |
| 79 | 87 | 91 | " | " |
| 80 | 84 | 86 | " | " |
| 81 | 100 | 100 | " | " |
| 82 | 100 | 100 | " | " |
| 83 | 100 | 100 | " | " |
| 84 | 100 | 100 | " | " |
| 85 | 100 | 100 | " | " |
| 86 | 100 | 100 | " | " |
| 87 | 87 | 92 | " | " |
| 88 | 85 | 90 | " | " |
| 89 | 90 | 100 | " | " |
| 90 | 89 | 96 | " | " |
| 91 | 100 | 100 | " | " |
| 92 | 100 | 100 | " | " |
| 93 | 100 | 100 | " | " |
| 94 | 100 | 100 | " | " |
| 95 | 100 | 100 | " | " |
| 96 | 100 | 100 | " | " |
| 97 | 100 | 100 | " | " |
| 98 | 100 | 100 | " | " |
| 99 | 100 | 100 | " | " |
| 100 | 100 | 100 | " | " |
| 101 | 100 | 100 | " | " |
| 102 | 100 | 100 | " | " |
| 103 | 100 | 100 | " | " |
| 104 | 100 | 100 | " | " |
| 105 | 100 | 100 | " | " |
| 106 | 100 | 100 | " | " |
| 107 | 100 | 100 | " | " |
| 108 | 100 | 100 | " | " |
| 109 | 100 | 100 | " | " |
| 110 | 100 | 100 | " | " |
| 111 | 100 | 100 | " | " |
| 112 | 100 | 100 | " | " |
| 113 | 100 | 100 | " | " |
| 114 | 100 | 100 | " | " |
| 115 | 100 | 100 | " | " |
| 116 | 100 | 100 | " | " |
| 117 | 100 | 100 | " | " |
| 118 | 100 | 100 | " | " |
| 119 | 100 | 100 | " | " |
| 120 | 100 | 100 | " | " |
| 121 | 100 | 100 | " | " |
| 122 | 100 | 100 | " | " |
| 123 | 100 | 100 | " | " |
| 124 | 80 | 84 | " | " |
| 125 | 81 | 80 | " | " |
| 126 | 98 | 96 | " | " |
| 127 | 100 | 98 | " | " |
| 128 | 93 | 100 | " | " |
| 129 | 90 | 99 | " | " |
| 130 | 100 | 100 | " | " |
| 131 | 100 | 100 | " | " |
| 132 | 100 | 100 | " | " |
| 133 | 100 | 100 | " | " |
| 134 | 100 | 100 | " | " |
| 135 | 100 | 100 | " | " |
| 136 | 96 | 100 | " | " |
| 137 | 94 | 96 | " | " |
| 138 | 100 | 100 | " | " |
| 139 | 95 | 92 | " | " |
| 140 | 92 | 88 | " | " |

TABLE 2-continued

| Compound No. | Control (%) Concentration of active ingredient compound sprayed (ppm) | | Phytotoxicity | |
|---|---|---|---|---|
| | Leaf rust on wheat 50 | Powdery mildew on cucumber 50 | Wheat | Cucumber |
| 141 | 91 | 93 | " | " |
| 142 | 100 | 100 | " | " |
| 143 | 90 | 98 | " | " |
| 144 | 98 | 100 | " | " |
| 145 | 100 | 100 | " | " |
| 146 | 100 | 100 | " | " |
| 147 | 100 | 100 | " | " |
| 148 | 97 | 92 | " | " |
| 149 | 93 | 90 | " | " |
| 150 | 100 | 100 | " | " |
| 151 | 99 | 100 | " | " |
| 152 | 100 | 100 | " | " |
| 153 | 94 | 100 | " | " |
| 154 | 91 | 96 | " | " |
| 155 | 90 | 87 | " | " |
| 156 | 100 | 100 | " | " |
| 157 | 89 | 91 | " | " |
| 158 | 92 | 88 | " | " |
| 159 | 100 | 100 | " | " |
| 160 | 100 | 100 | " | " |
| 161 | 100 | 100 | " | " |
| 162 | 98 | 97 | " | " |
| 163 | 99 | 100 | " | " |
| 164 | 87 | 96 | " | " |
| 165 | 86 | 96 | " | " |
| 166 | 100 | 100 | " | " |
| 167 | 100 | 100 | " | " |
| 168 | 94 | 100 | " | " |
| 169 | 92 | 93 | " | " |
| 170 | 90 | 88 | " | " |
| 171 | 80 | 85 | " | " |
| 172 | 86 | 87 | " | " |
| 173 | 98 | 100 | " | " |
| 174 | 98 | 100 | " | " |
| 175 | 92 | 96 | " | " |
| 176 | 83 | 88 | " | " |
| 177 | 90 | 91 | " | " |
| 178 | 89 | 90 | " | " |
| 179 | 92 | 92 | " | " |
| 180 | 99 | 100 | " | " |
| 181 | 100 | 100 | " | " |
| 182 | 100 | 100 | " | " |
| 183 | 100 | 100 | " | " |
| 184 | 99 | 100 | " | " |
| 185 | 100 | 100 | " | " |
| 186 | 100 | 100 | " | " |
| 187 | 100 | 100 | " | " |
| 188 | 100 | 100 | " | " |
| 189 | 100 | 100 | " | " |
| 190 | 100 | 100 | " | " |
| 191 | 99 | 100 | " | " |
| 192 | 89 | 95 | " | " |
| 193 | 100 | 100 | " | " |
| 194 | 93 | 95 | " | " |
| 195 | 100 | 100 | " | " |
| 196 | 82 | 86 | " | " |
| 197 | 90 | 92 | " | " |
| 198 | 87 | 85 | " | " |
| 199 | 85 | 82 | " | " |
| 200 | 100 | 100 | " | " |
| 201 | 100 | 100 | " | " |
| 202 | 100 | 100 | " | " |
| 203 | 100 | 100 | " | " |
| 204 | 100 | 100 | " | " |
| 205 | 81 | 80 | " | " |
| 206 | 90 | 86 | " | " |
| 207 | 88 | 89 | " | " |
| 208 | 89 | 94 | " | " |
| 209 | 80 | 83 | " | " |
| 210 | 92 | 96 | " | " |
| 211 | 100 | 100 | " | " |
| 212 | 100 | 100 | " | " |
| 213 | 100 | 100 | " | " |
| 214 | 100 | 100 | " | " |
| 215 | 98 | 100 | " | " |
| 216 | 82 | 86 | " | " |
| 217 | 80 | 82 | " | " |
| 218 | 93 | 95 | " | " |
| 219 | 90 | 90 | " | " |
| 220 | 92 | 86 | " | " |
| 221 | 90 | 92 | " | " |
| 222 | 87 | 85 | " | " |
| 223 | 85 | 82 | " | " |
| 224 | 82 | 86 | " | " |
| 225 | 84 | 88 | " | " |
| 226 | 82 | 89 | " | " |
| 227 | 81 | 84 | " | " |
| 228 | 83 | 86 | " | " |
| 229 | 88 | 92 | " | " |
| 230 | 100 | 96 | " | " |
| 231 | 100 | 100 | " | " |
| 232 | 100 | 100 | " | " |
| 233 | 100 | 100 | " | " |
| 234 | 100 | 100 | " | " |
| 235 | 100 | 100 | " | " |
| 236 | 100 | 92 | " | " |
| 237 | 100 | 100 | " | " |
| 238 | 100 | 100 | " | " |
| 239 | 100 | 98 | " | " |
| 240 | 100 | 96 | " | " |
| 241 | 100 | 100 | " | " |
| 242 | 98 | 94 | " | " |
| 243 | 100 | 99 | " | " |
| 244 | 100 | 100 | " | " |
| Comparative compound A | 75 | 73 | | |
| Comparative compound B | 78 | 78 | " | " |
| Comparative compound C | 85 | — | " | |
| Comparative compound D | — | 86 | | " |
| No treatment | 0 | 0 | — | — |

Notes:

Comparative compound A: 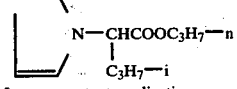

(a compound described in Japanese patent application unexamined prepublication "Kokai" Sho 52-27767)

Comparative compound B: 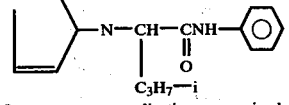

(a compound described in Japanese patent application unexamined prepublication "Kokai" Sho 52-27767)

Comparative compound C: Ethylene-bis(dithiocarbamic acid) manganese salt (known under the tradename "Manneb")

Comparative compound D: Dithiocarbonic acid S,S—6-methylquinoxaline-2,3-di-yl ester (known under the tradename "Quinomethionate")

EXAMPLE 29

This Example illustrates tests of controlling leaf rust in wheat in preventative treatment when the test compound is applied at low concentrations.

The effects of the test compounds against leaf rust disease in wheat were estimated in the same manner as in Example 27, while the test compounds were applied at low concentrations as indicated in Table 3 below. The tests were conducted with three replicates. The test results (expressed as averaged % Control) are given in Table 3.

TABLE 3

| | Control (%) Concentration of active ingredient compound sprayed (ppm) | | |
|---|---|---|---|
| Compound No. | 25 | 12.5 | 6.25 |
| 7 | 100 | 92 | 84 |
| 16 | 100 | 98 | 86 |
| 28 | 100 | 92 | 81 |
| 52 | 100 | 98 | 86 |
| 70 | 100 | 96 | 92 |
| 71 | 100 | 99 | 91 |
| 85 | 100 | 98 | 92 |
| 86 | 100 | 92 | 86 |
| 95 | 100 | 100 | 98 |
| 99 | 100 | 100 | 94 |
| 102 | 100 | 100 | 98 |
| 103 | 100 | 100 | 97 |
| 106 | 100 | 100 | 94 |
| 108 | 100 | 100 | 96 |
| 115 | 100 | 100 | 99 |
| 118 | 100 | 100 | 96 |
| 120 | 100 | 100 | 95 |
| 121 | 100 | 100 | 96 |
| 131 | 100 | 100 | 92 |
| 134 | 100 | 100 | 95 |
| 138 | 100 | 98 | 89 |
| 152 | 100 | 98 | 91 |
| 159 | 98 | 92 | 80 |
| 181 | 100 | 98 | 90 |
| 182 | 98 | 99 | 92 |
| 186 | 100 | 100 | 98 |
| 187 | 100 | 100 | 95 |
| 189 | 100 | 100 | 97 |
| 190 | 100 | 100 | 95 |
| 103 | 100 | 100 | 92 |
| 195 | 99 | 94 | 86 |
| 200 | 100 | 92 | 86 |
| 203 | 100 | 100 | 99 |
| 212 | 100 | 100 | 97 |
| 213 | 100 | 100 | 92 |
| 214 | 100 | 100 | 91 |
| 231 | 100 | 100 | 100 |
| 232 | 100 | 100 | 100 |
| 233 | 100 | 100 | 100 |
| 235 | 100 | 100 | 100 |
| 236 | 100 | 100 | 100 |
| 238 | 100 | 100 | 100 |
| 240 | 100 | 99 | 96 |
| 241 | 100 | 100 | 98 |
| 243 | 100 | 99 | 97 |
| 244 | 100 | 100 | 99 |
| Comparative compound A | 51 | 32 | 5 |
| Comparative compound B | 62 | 38 | 10 |
| Comparative compound C | 72 | 55 | 20 |

EXAMPLE 30

This Example illustrates tests of controlling leaf rust in wheat in curative treatment.

The procedures of Example 27 for controlling the wheat leaf rust disease were used but except that the spraying of the composition under test was made one day after the inoculation of the wheat leaf rust fungi on the wheat leave. The test results obtained are set out in Table 4 below.

TABLE 4

| Compound No. | Concentration of test compound sprayed (ppm) | Control (%) | Phyto-toxicity |
|---|---|---|---|
| 7 | 50 | 92 | 0 |
| 11 | " | 99 | " |
| 16 | " | 100 | " |
| 28 | " | 100 | " |
| 32 | " | 98 | " |
| 35 | " | 96 | " |
| 43 | " | 96 | " |
| 52 | " | 100 | " |
| 58 | " | 93 | " |
| 70 | " | 100 | " |
| 71 | " | 100 | " |
| 73 | " | 100 | " |
| 75 | " | 96 | " |
| 83 | " | 100 | " |
| 85 | " | 100 | " |
| 86 | " | 100 | " |
| 91 | " | 91 | " |
| 94 | " | 100 | " |
| 95 | " | 100 | " |
| 96 | " | 100 | " |
| 99 | " | 100 | " |
| 102 | " | 100 | " |
| 103 | " | 100 | " |
| 106 | " | 100 | " |
| 108 | " | 100 | " |
| 115 | " | 100 | " |
| 118 | " | 100 | " |
| 120 | " | 100 | " |
| 121 | " | 100 | " |
| 130 | " | 100 | " |
| 131 | " | 100 | " |
| 134 | " | 100 | " |
| 138 | " | 100 | " |
| 152 | " | 100 | " |
| 159 | " | 100 | " |
| 166 | " | 93 | " |
| 167 | " | 97 | " |
| 181 | " | 100 | " |
| 182 | " | 100 | " |
| 186 | " | 100 | " |
| 187 | " | 100 | " |
| 189 | " | 100 | " |
| 190 | " | 100 | " |
| 193 | " | 100 | " |
| 195 | " | 100 | " |
| 200 | " | 100 | " |
| 203 | " | 100 | " |
| 212 | " | 100 | " |
| 213 | " | 100 | " |
| 214 | " | 100 | " |
| Comparative compound A | 50 | 40 | 0 |
| Comparative compound B | " | 47 | " |
| Comparative compound C | " | 40 | " |
| No treatment | — | 0 | — |

EXAMPLE 31

This Example illustrates tests of controlling powdery mildew in cucumber when the test compound was applied at low concentrations.

The effects of the test compounds for controlling the cucumber powdery mildew disease were estimated in the same manner as in Example 28, while the test compounds were applied at low concentrations as indicated in Table 5 below. The test results obtained (expressed as averaged % Control) are tabulated in Table 5 below.

TABLE 5

| | Control (%) Concentration of test compound sprayed (ppm) | | |
|---|---|---|---|
| Compound No. | 20 | 5 | 1.25 |
| 16 | 100 | 86 | 53 |
| 71 | 100 | 96 | 71 |

TABLE 5-continued

| Compound No. | Control (%) Concentration of test compound sprayed (ppm) | | |
|---|---|---|---|
| | 20 | 5 | 1.25 |
| 85 | 100 | 98 | 70 |
| 99 | 100 | 100 | 66 |
| 102 | 100 | 100 | 72 |
| 103 | 100 | 100 | 65 |
| 106 | 100 | 100 | 68 |
| 108 | 100 | 100 | 63 |
| 115 | 100 | 100 | 83 |
| 118 | 100 | 100 | 76 |
| 120 | 100 | 100 | 62 |
| 131 | 100 | 100 | 82 |
| 138 | 100 | 100 | 70 |
| 146 | 100 | 98 | 50 |
| 161 | 100 | 99 | 54 |
| 167 | 100 | 84 | 60 |
| 181 | 100 | 97 | 51 |
| 182 | 100 | 100 | 56 |
| 184 | 100 | 98 | 59 |
| 186 | 100 | 99 | 96 |
| 187 | 100 | 92 | 88 |
| 189 | 100 | 100 | 92 |
| 190 | 100 | 99 | 90 |
| 193 | 100 | 98 | 86 |
| 195 | 100 | 86 | 58 |
| 200 | 100 | 98 | 58 |
| 201 | 100 | 92 | 50 |
| 212 | 100 | 96 | 72 |
| 214 | 100 | 90 | 66 |
| 232 | 100 | 93 | 65 |
| 233 | 100 | 96 | 75 |
| 234 | 100 | 93 | 55 |
| 238 | 100 | 100 | 98 |
| 241 | 100 | 87 | 68 |
| 244 | 100 | 100 | 73 |
| Comparative compound A | 51 | 23 | 0 |
| Comparative compound B | 56 | 31 | 5 |
| Comparative compound D | 61 | 25 | 0 |

EXAMPLE 32

This Example illustrates test of controlling brown spot in rice.

Rice plants (variety: Asahi) were grown in soil in 9 cm-diameter porous pots in a greenhouse. At the four true-leaf stage, the rice plants were sprayed with the composition under test which was prepared by diluting the wettable powder of Example 21 with water to a concentration of the active compound as indicated in Table 6 below. One day after the treatment, the treated rice plants were sprayed for inoculation with a suspension of conidiospores of rice brown spot fungi (*Cochliobolus miyabeanus*). 5 Days after inoculation, the number of the lesions on the fourth leaf developed by infection was counted. The degree of control (%) was then evaluated according to the under-mentioned equation. Degree of phyto-toxicity of the test compound was also estimated by the same grading as in Example 27. The test results are set out in Table 6 below.

$$\text{Control (\%)} = \left(1 - \frac{\text{Number of lesions developed by infection in a treated leaf}}{\text{Number of lesions developed by infection in a non-treated leaf}}\right) \times 100$$

TABLE 6

| Compound No. | Concentration of test compound sprayed (ppm) | Control (%) | Phyto-toxicity |
|---|---|---|---|
| 5 | 100 | 96 | 0 |
| 7 | " | 100 | " |
| 9 | " | 95 | " |
| 11 | " | 93 | " |
| 15 | " | 91 | " |
| 16 | " | 100 | " |
| 17 | 100 | 98 | 0 |
| 26 | " | 100 | " |
| 27 | " | 100 | " |
| 35 | " | 96 | " |
| 40 | " | 100 | " |
| 52 | " | 98 | " |
| 58 | " | 88 | " |
| 71 | " | 99 | " |
| 73 | " | 98 | " |
| 81 | " | 93 | " |
| 83 | " | 100 | " |
| 85 | " | 98 | " |
| 86 | " | 96 | " |
| 87 | " | 94 | " |
| 93 | " | 100 | " |
| 94 | " | 100 | " |
| 95 | " | 100 | " |
| 96 | " | 94 | " |
| 99 | " | 100 | " |
| 100 | " | 100 | " |
| 102 | " | 100 | " |
| 103 | " | 98 | " |
| 115 | " | 96 | " |
| 128 | " | 100 | " |
| 130 | " | 100 | " |
| 131 | " | 98 | " |
| 138 | " | 96 | " |
| 145 | " | 89 | " |
| 152 | " | 100 | " |
| 159 | " | 100 | " |
| 161 | " | 98 | " |
| 167 | " | 90 | " |
| 181 | " | 98 | " |
| 182 | " | 100 | " |
| 184 | " | 100 | " |
| 191 | " | 97 | " |
| 195 | " | 90 | " |
| 200 | " | 93 | " |
| 211 | " | 93 | " |
| 212 | " | 90 | " |
| 216 | " | 90 | " |
| 230 | " | 100 | " |
| 239 | " | 98 | " |
| 240 | " | 100 | " |
| 243 | " | 95 | " |
| Comparative compound A | 100 | 45 | |
| Comparative compound B | " | 36 | |
| Comparative compound E | " | 84 | |
| No treatment | — | 0 | — |

Note: Comparative compound E: 2,4-Dichloro-6-(O—chloroanilino)-1,3,5-triazine (Triazine).

EXAMPLE 33

This Example sets out the tests of estimating the activities of the test compounds against various kinds of plant-pathogenic fungi.

A compound of this invention was dissolved in acetone, and 1 ml of the resultant solution was admixed with 20 ml of an incubation agar medium at 60° C. (for incubation of fungi: PSA-medium, pH 5.8) in a Petri dish of 9 cm diameter to prepare an agar plate containing the test compound at a predetermined concentration as indicated in Table 7 below. The Petri dish, without the upper cover, was allowed to stand overnight to evaporate acetone off, and the agar plate so prepared was inoculated with a loopful amount of a suspension of spores of the test microorganism which were previously incubated on agar slant medium. After incubation for 48 hours at 24° C., the conditions of the growth of the test microorganisms were assessed by the following grading. The results are listed in Table 7 below.

Grades of growth of the fungi:
- —: No growth at all.
- ⊥: Formation of a few colonies was observed in the inoculated region of the agar plate where the spore suspension had been applied, and the growth was greatly suppressed.
- +: Formation of many colonies was observed in the inoculated region of the agar plate where the spore suspension had been applied, but the growth was so suppressed not to cover the whole surface of said region.
- ++: Growth covered the whole surface of the inoculated region of the agar plate where the spore suspension had been applied, but the growth was still poor.
- +++: Growth covered the whole surface of the inoculated region of the agar plate where the spore suspension had been applied, and the growth was good.

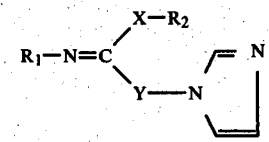 [I]

wherein
$R_1$ is naphthyl group, an arylalkyl group, a cycloalkyl group, a cycloalkylalkyl group, an alkyl group, a lower alkenyl group, a lower alkoxy-lower alkyl group, a phenylthio-lower alkyl group or phenyl group; the phenyl group being unsubstituted or substituted with 1 to 5 substituents which is or are the same or different from each other and selected from a halogen atom, nitro group, cyano group, a lower alkyl group, a lower alkenyl group, a halogenated lower alkyl group, a lower alkoxyl group, a lower alkenyloxy group, a lower alkylthio group, a lower alkylsulfinyl group, a lower alkylsulfonyl group, a lower alkylcarbonyl group, phenyl group, phenoxy group, a halogen-substituted phenoxy group, phenylthio group, a lower alkyl-substituted phenylthio group and a nitro-substituted phenylthio group; $R_2$ is a saturated alkyl group, an

TABLE 7

| Compound No. | A | B | C | D | E | F | G | H | I | J | K |
|---|---|---|---|---|---|---|---|---|---|---|---|
| 16 | 10 | — | — | ⊥ | — | + | — | ⊥ | — | ⊥ | — |
| 28 | " | — | — | ⊥ | ⊥ | + | — | — | " | ⊥ | — |
| 32 | " | — | — | ⊥ | + | + | — | ⊥ | — | ⊥ | — |
| 43 | " | — | — | ⊥ | — | + | — | — | — | — | — |
| 85 | " | — | — | — | — | + | — | — | — | — | — |
| 86 | " | — | — | — | — | ⊥ | — | — | — | — | — |
| 95 | " | ⊥ | — | — | — | + | — | — | — | ⊥ | — |
| 99 | " | — | — | — | — | ⊥ | — | — | — | — | — |
| 102 | " | — | — | — | — | + | — | — | — | — | — |
| 106 | " | — | ⊥ | — | — | ⊥ | — | ⊥ | — | — | ⊥ |
| 115 | " | — | — | — | — | + | — | — | — | — | — |
| 118 | " | — | — | — | — | ⊥ | — | — | — | — | — |
| 120 | " | — | — | ⊥ | — | ⊥ | — | — | — | — | — |
| 131 | " | — | — | — | — | + | — | ⊥ | — | — | — |
| 134 | " | — | — | — | — | ⊥ | — | — | — | — | — |
| 161 | " | — | ⊥ | ⊥ | — | ++ | — | — | — | ⊥ | ⊥ |
| 167 | " | — | ⊥ | — | — | ++ | — | — | — | — | ⊥ |
| 182 | " | — | ⊥ | ⊥ | — | + | — | — | — | ⊥ | ⊥ |
| 186 | " | — | ⊥ | ⊥ | — | + | — | — | — | ⊥ | — |
| 200 | " | — | — | — | — | ⊥ | — | — | — | — | — |
| 203 | " | — | ⊥ | ⊥ | — | ++ | — | — | — | ⊥ | ⊥ |
| 212 | " | — | — | ⊥ | ⊥ | + | — | — | — | ⊥ | — |
| 230 | " | — | — | — | — | + | — | — | — | — | — |
| 234 | " | — | — | ⊥ | — | + | — | — | — | ⊥ | — |
| 235 | " | — | — | — | — | + | — | — | — | — | ⊥ |
| 236 | " | — | — | ⊥ | — | + | — | — | — | — | — |
| 239 | " | — | — | ⊥ | — | + | — | — | — | — | — |
| 240 | " | — | — | ⊥ | — | ++ | — | — | ⊥ | — | — |
| 241 | " | — | — | — | — | + | — | — | — | — | — |
| 242 | " | — | — | ⊥ | — | ++ | — | — | — | — | — |
| 243 | " | — | — | — | — | ⊥ | — | — | — | — | — |
| No addition | 0 | +++ | +++ | +++ | +++ | +++ | +++ | +++ | +++ | +++ | +++ |

Note:
A - Concentration of test compound (ppm).
B - *Cladosporium fulvum* in tomato.
C - *Gibberella fujikuroi* in rice.
D - *Glomerella cingulata* in vine.
E - *Alternaria kikuchiana* in pear.
F - *Valsa mali* in apple.
G - *Piricularia oryzae* in rice.
H - *Cochliobolus miyabeanus* in rice.
I - *Cercospora beticola* in beet.
J - *Colletotrichum lagenarium* in cucumber.
K - *Fusarium oxysporum* in cucumber.

What we claim is:
1. An imidazole derivative of the general formula unsaturated alkyl group, a lower alkoxy-lower alkyl group, a lower alkylthio-lower alkyl group, a phenoxy-lower alkyl group, a phenylthio-lower alkyl group, a mono- or di-lower alkylamino-lower alkyl group, a lower alkyl group substituted with a group —N(CH$_2$)$_n$ where n is an integer of 2 to 6, a lower alkylcarbonyl group, phenylcarbonyl group, a cycloalkyl group, a cycloalkylalkyl group, a halogenated lower alkyl group, a cyano-lower alkyl group, a lower alkoxycarbonyl-lower alkyl group, a lower alkylthiocarbonyl-lower alkyl group, an arylalkyl group, a lower alkylcarbonyl-lower alkyl group, a phenylcarbonyl-lower alkyl group, naphthyl group, furfuryl group or phenyl group; the latter phenyl group being unsubstituted or substituted with a substitutent which is selected from a halogen atom, nitro group, cyano group and a lower alkyl group;

X is an oxygen atom or a sulfur atom; and

Y is a straight or branched saturated alkylene group or unsaturated alkylene group, the saturated alkylene group being unsubstituted or substituted with a halogen group, a lower alkoxyl group, cyano group, phenyl group, a halogen-substituted phenyl group, a nitro-substituted phenyl group, a lower alkyl-substituted phenyl group and/or trifluoromethyl-substituted phenyl group, and a salt of said imidazole derivative.

2. An imidazole derivative as claimed in claim 1 which is of the formula

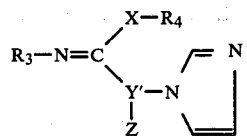 [Ia]

wherein

R$_3$ is naphthyl group, a phenyl-(C$_1$-C$_4$)alkyl group, a dichlorophenyl-(C$_1$-C$_4$)alkyl group, a (C$_5$-C$_6$)cycloalkyl group, a (C$_5$-C$_6$)cycloalkyl-(C$_1$-C$_4$)alkyl group, a (C$_1$-C$_{10}$) alkyl group, a (C$_2$-C$_4$)alkenyl group, a (C$_1$-C$_4$)alkoxy-(C$_1$-C$_4$)alkyl group, a phenylthio-(C$_1$-C$_4$)alkyl group, phenyl group, a chlorophenyl group, a fluorophenyl group, a bromophenyl group, a nitrophenyl group, a cyanophenyl group, a trifluoromethylphenyl group, a dichlorophenyl group, a dibromophenyl group, a difluorophenyl group, a bromochlorophenyl group, a chlorofluorophenyl group, a trifluromethylchlorophenyl group, a trichlorophenyl group, a dichlorodimethylphenyl group, a trichloro-dimethylphenyl group, a chloro-methoxyphenyl group, a chloro-methylphenyl group, a (C$_1$-C$_4$)alkylphenyl group, a di-(C$_1$-C$_4$)alkylphenyl group, a (C$_2$-C$_4$)alkenylphenyl group, a (C$_2$-C$_4$)alkenyloxyphenyl group, a (C$_1$-C$_4$)alkoxyphenyl group, a di-(C$_1$-C$_4$)alkoxyphenyl group, a (C$_1$-C$_4$)alkylthiophenyl group, a (C$_1$-C$_4$)alkylsulfinylphenyl group, a (C$_1$-C$_4$)alkylsulfonylphenyl group, a (C$_1$-C$_4$)alkylcarbonylphenyl group, diphenyl group, phenoxyphenyl group, a chlorophenoxyphenyl group, a phenylthiophenyl group, a (C$_1$-C$_4$)alkylphenylthiophenyl group or a nitrophenylthiophenyl group, R$_4$ is a (C$_1$-C$_{10}$)alkyl group, a (C$_2$-C$_4$)alkenyl group, a (C$_2$-C$_4$)alkynyl group, a (C$_1$-C$_4$)alkoxy-(C$_1$-C$_4$)alkyl group, a (C$_5$-C$_6$)cycloalkyl-(C$_1$-C$_4$)alkyl group, a (C$_1$-C$_4$)alkylthio-(C$_1$-C$_4$)alkyl group, a phenyl-(C$_1$-C$_4$)alkyl group, a phenoxy-(C$_1$-C$_4$)alkyl group, a dichlorophenoxy-(C$_1$-C$_4$)alkyl group, a phenylthio-(C$_1$-C$_4$)alkyl group, a (C$_1$-C$_4$)alkylamino-(C$_1$-C$_4$)alkyl group, a di-(C$_1$-C$_4$)alkylamino-(C$_1$-C$_4$)alkyl group, a pyrrolyl-(C$_1$-C$_4$)alkyl group, a chloro-(C$_1$-C$_4$)alkyl group, a cyano-(C$_1$-C$_4$)alkyl group, a (C$_1$-C$_4$)alkoxycarbonyl-(C$_1$-C$_4$)alkyl group, a (C$_1$-C$_4$)alkylthiocarbonyl-(C$_1$-C$_4$)alkyl group, a (C$_1$-C$_4$)alkylcarbonyl-(C$_1$-C$_4$)alkyl group, a phenylcarbonyl-(C$_1$-C$_4$)alkyl group, a (C$_5$-C$_6$)cycloalkyl group, benzyl group, a chlorobenzyl group, a dichlorobenzyl group, a fluorobenzyl group, a methylbenzyl group, a dimethylbenzyl group, a methylbenzylethyl group, naphthyl group, furfuryl group, phenyl group, a chlorophenyl group, a dichlorophenyl group, a cyanophenyl group, a nitrophenyl group, a (C$_1$-C$_4$)alkylphenyl group, a (C$_1$-C$_4$)alkylcarbonyl group, or benzoyl group, X is an oxygen atom or a sulfur atom;

Y' is a (C$_1$-C$_4$)alkylene group or a (C$_2$-C$_4$)alkenylene group; and

Z is a hydrogen atom, a (C$_1$-C$_6$)alkyl group, a (C$_1$-C$_4$)alkoxy-(C$_1$-C$_4$)alkyl group, a cyano-(C$_1$-C$_4$)alkyl group, a (C$_2$-C$_4$)alkenyl group, phenyl group, a chlorophenyl group, a dichlorophenyl group, a methylphenyl group, a trifluoromethylphenyl group, a nitrophenyl group, benzyl group, a chlorobenzyl group or a dichlorobenzyl group; and a salt of said imidazole derivative.

3. An imidazole derivative as claimed in claim 1 which is of the formula

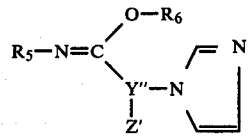 [Ib]

wherein

R$_5$ is phenyl group, a chlorophenyl group, a bromophenyl group, a nitrophenyl group, a trifluoromethylphenyl group, a dichlorophenyl group, a bromochlorophenyl group, a chlorofluorophenyl group, a trifluoromethylchlorophenyl group, a trichlorophenyl group, a dichlorodimethylphenyl group, a trichloro-dimethylphenyl group, a chloromethoxyphenyl group, a chloro-methylphenyl group, a (C$_1$-C$_4$)alkylphenyl group, a di-(C$_1$-C$_4$)alkylphenyl group, a (C$_2$-C$_4$)alkenyloxyphenyl group, a (C$_1$-C$_4$)alkoxyphenyl group, a di-(C$_1$-C$_4$)alkoxyphenyl group, a methylsulfonylphenyl group, an acetylphenyl group, a phenoxyphenyl group, or a nitrophenylthiophenyl group;

R$_6$ is a (C$_1$-C$_{10}$)alkyl group, a (C$_2$-C$_4$)alkenyl group, a (C$_1$-C$_4$)alkoxy-(C$_1$-C$_4$)alkyl group, a methylthio-(C$_1$-C$_4$)alkyl group, a dichlorophenoxy-(C$_1$-C$_4$)alkyl group, a phenylthio-(C$_1$-C$_4$)alkyl group, cyclohexyl group, an ethoxycarbonyl-(C$_1$-C$_4$)alkyl group, benzyl group, a chlorobenzyl group, a dichlorobenzyl group, naphthyl group, furfuryl group, phenyl group, a chlorophenyl group, a dichlorophenyl group, a cyanophenyl group, a nitrophenyl group, or a (C$_1$-C$_4$)alkylphenyl group, Y'' is a linear (C$_2$-C$_4$)alkylene group, Z' is a hydrogen atom, a (C$_1$-C$_6$)alkyl group, a (C$_2$-C$_4$)alkenyl group, phenyl group, a chlorophenyl group, a dichlorophenyl group, a methylphenyl group, a nitrophenyl group, or benzyl group, and a salt of said imidazole derivative.

4. An imidazole derivative as claimed in claim 1 which is of the formula

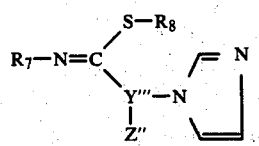

[Ic]

wherein $R_7$ is phenyl group, a chlorophenyl group, a fluorophenyl group, a bromophenyl group, or nitrophenyl group, a cyanophenyl group, a trifluoromethylphenyl group, a dichlorophenyl group, a dibromophenyl group, a bromochlorophenyl group, a chlorofluorophenyl group, a trifluoromethylchlorophenyl group, a trichlorophenyl group, a dichloro-dimethylphenyl group, a trichloro-dimethylphenyl group, a chloro-methoxyphenyl group, a chloro-methylphenyl group, a ($C_1$-$C_4$)alkylphenyl group, a di-($C_1$-$C_4$)alkylphenyl group, a ($C_2$-$C_4$)alkenyphenyl group, a ($C_1$-$C_4$)alkoxyphenyl group, a di-($C_1$-$C_4$)alkoxyphenyl group, a methylthiophenyl group, a methylsulfinylphenyl group, a methylsulfonylphenyl group, an acetylphenyl group, diphenyl group, a phenoxyphenyl group, a chlorophenoxyphenyl group, a phenylthiophenyl group or a methylphenylthiophenyl group;

$R_8$ is a ($C_1$-$C_{10}$)alkyl group, a ($C_2$-$C_4$)alkenyl group, a ($C_2$-$C_4$)alkynyl group, a ($C_1$-$C_4$)alkoxy-($C_1$-$C_4$)alkyl group, a methylthio-($C_1$-$C_4$)alkyl group, a phenoxy-($C_1$-$C_4$)alkyl group, a phenylthio-($C_1$-$C_4$)alkyl group, a ($C_1$-$C_4$)alkylamino-($C_1$-$C_4$)alkyl group, a pyrrolyl-($C_1$-$C_4$)alkyl group, a ($C_1$-$C_4$)alkylcarbonyl group, a ($C_5$-$C_6$)cycloalkyl group, a chloro($C_1$-$C_4$)alkyl group, a cyano-($C_1$-$C_4$)alkyl group, a ($C_1$-$C_4$)alkylthiocarbonyl-($C_1$-$C_4$)alkyl group, benzyl group, a chlorobenzyl group, a fluorobenzyl group, a dichlorobenzyl group, a methylbenzyl group, a methylbenzylethyl group, an acetyl-($C_1$-$C_4$)alkyl group, benzoyl group, a phenylcarbonyl-($C_1$-$C_4$)alkyl group or phenyl group;

$Y'''$ is a linear ($C_1$-$C_4$)alkylene group or a linear ($C_2$-$C_4$)alkenylene group; and $Z''$ is a hydrogen atom, a ($C_1$-$C_6$)alkyl group, a ($C_1$-$C_4$)alkoxy-($C_1$-$C_4$)alkyl group, a cyano-($C_1$-$C_4$)alkyl, a ($C_2$-$C_4$)alkenyl, phenyl group, a chlorophenyl group, a dichlorophenyl group, a methylphenyl group, benzyl group, a chlorobenzyl group or a dichlorobenzyl group; and a salt of said imidazole derivative.

5. An imidazole derivative as claimed in claim 1 which is of the formula

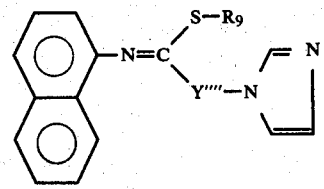

[Id]

wherein $R_9$ is a ($C_1$-$C_4$)alkyl group, a phenyl-($C_1$-$C_4$)alkyl group or a chloro-($C_1$-$C_4$)alkyl group; and $Y''''$ is a linear or branched ($C_1$-$C_4$)alkylene group, and a salt of the said imidazole derivative.

6. An imidazole derivative as claimed in claim 1 which is of the formula

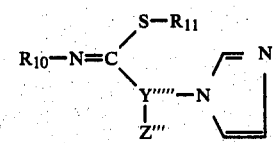

[Ie]

wherein $R_{10}$ is a ($C_5$-$C_6$)cycloalkyl group or a ($C_1$-$C_4$)alkyl group which is unsubstituted or substituted with phenyl group, a dichlorophenyl group, a ($C_2$-$C_4$)alkenyl group, a ($C_1$-$C_4$)alkoxy group or phenylthio group;

$R_{11}$ is furfuryl or ($C_1$-$C_4$)alkyl group which is unsubstituted or substituted with phenyl group, a di-($C_1$-$C_4$)alkylamino group or a ($C_5$-$C_6$)cycloalkyl group;

$Y'''''$ is a ($C_1$-$C_4$)alkylene group; and $Z'''$ is a hydrogen atom, a ($C_1$-$C_6$)alkyl group, a chlorobenzyl group or a trifluoromethylphenyl group; and a salt of said imidazole derivative.

7. An imidazole derivative as claimed in claim 1, which is the compound of the formula

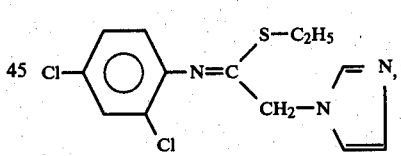

(Compound No. 94)

the compound of the formula (Compound No. 102)

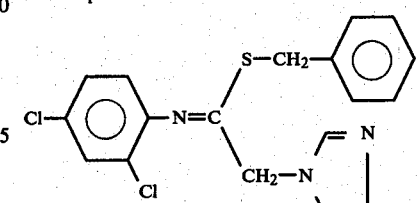

the compound of the formula (Compound No. 115)

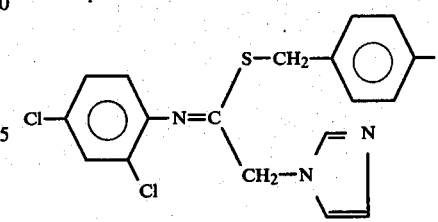

-continued the compound of the formula (Compound No. 134)

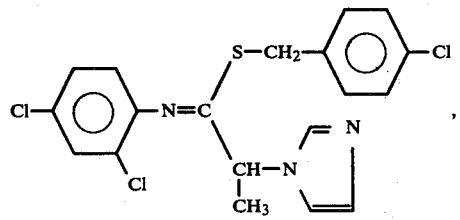

the compound of the formula (Compound No. 186)

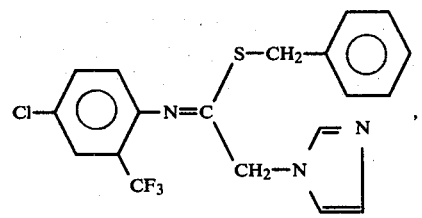

-continued the compound of the formula (Compound No. 238)

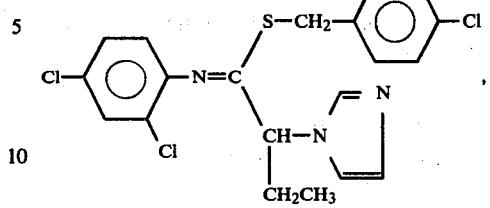

or the compound of the formula (Compound No. 241)

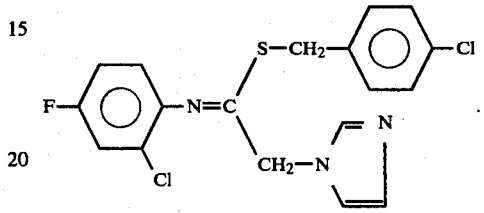

8. A fungicidal composition comprising as the active ingredient a fungicidally effective amount of an imidazole derivative as defined in claim 1, or a salt thereof, in association with an acceptable carrier for the active ingredient.

9. A method of combating the fungal pests of plants, which comprises treating plants, seeds or trees with a fungicidally effective amount of an imidazole derivative as defined in claim 1 or a salt thereof.

* * * * *